(12) United States Patent
Chen et al.

(10) Patent No.: US 10,493,265 B2
(45) Date of Patent: Dec. 3, 2019

(54) MEDICAL LEADS AND TECHNIQUES FOR MANUFACTURING THE SAME

(71) Applicant: Medtronic, Inc., Minneapolis, MN (US)

(72) Inventors: Xingfu Chen, Lino Lakes, MN (US); Bernard Q. Li, Plymouth, MN (US); Richard T. Stone, Minneapolis, MN (US); Dale F. Seeley, Spring Park, MN (US); Alan Shi, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 744 days.

(21) Appl. No.: 14/209,799

(22) Filed: Mar. 13, 2014

(65) Prior Publication Data

US 2014/0277316 A1   Sep. 18, 2014

Related U.S. Application Data

(60) Provisional application No. 61/798,355, filed on Mar. 15, 2013.

(51) Int. Cl.
*A61N 1/05* (2006.01)
*A61N 1/375* (2006.01)
*H05K 13/00* (2006.01)

(52) U.S. Cl.
CPC ............ *A61N 1/05* (2013.01); *A61N 1/375* (2013.01); *H05K 13/00* (2013.01); *Y10T 29/49117* (2015.01)

(58) Field of Classification Search
CPC .................................. A61N 1/05; A61N 1/375
See application file for complete search history.

(56) References Cited

U.S. PATENT DOCUMENTS 4,602,637 A * 7/1986 Elmqvist ............... A61N 1/375
607/36
5,203,348 A   4/1993 Dahl et al.
(Continued)

FOREIGN PATENT DOCUMENTS

EP   1454651 A1   9/2004

OTHER PUBLICATIONS

Response to Office Action dated Jul. 8, 2015, from U.S. Appl. No. 14/206,650, filed Oct. 6, 2015, 10 pp.
(Continued)

*Primary Examiner* — William J Levicky
(74) *Attorney, Agent, or Firm* — Shumaker & Sieffert, P.A.

(57) ABSTRACT

In some examples, the disclosure relates to a medical device comprising a lead including an electrically conductive lead wire; and an electrode electrically coupled to the lead wire, the electrode including a first portion and a second portion, wherein the first portion defines an exposed outer surface of the electrode and is electrically coupled to the second portion along a first interface, wherein the second portion is electrically coupled to the lead wire along a second interface different from the first interface via welding to couple the lead wire to the electrode, wherein an electrical signal may be transferred between the lead wire and exposed outer surface of the first portion via the second portion, and wherein the first portion is formed from a first material having a first composition, and the second portion is formed from a second material having a second composition different from the first composition.

20 Claims, 24 Drawing Sheets

(56) References Cited

U.S. PATENT DOCUMENTS

| | | | |
|---|---|---|---|
| 5,603,732 A | 2/1997 | Dahl et al. | |
| 5,609,611 A | 3/1997 | Bolz et al. | |
| 5,632,770 A | 5/1997 | Schaldach | |
| 6,263,250 B1* | 7/2001 | Skinner | A61N 1/056 600/325 |
| 7,079,903 B2 | 7/2006 | O'Brien | |
| 7,603,169 B2 | 10/2009 | Kruger et al. | |
| 7,666,523 B2* | 2/2010 | Zhou | C25D 5/16 205/265 |
| 7,856,707 B2* | 12/2010 | Cole | A61N 1/05 29/825 |
| 8,000,808 B2 | 8/2011 | Hegland et al. | |
| 2005/0007718 A1 | 1/2005 | Stevenson et al. | |
| 2005/0084672 A1 | 4/2005 | O'Brien | |
| 2006/0167536 A1 | 7/2006 | Nygren et al. | |
| 2007/0239249 A1* | 10/2007 | Tockman | A61N 1/056 607/129 |
| 2008/0161886 A1 | 7/2008 | Stevenson et al. | |
| 2010/0075168 A1 | 4/2010 | Schaffer | |
| 2011/0072659 A1 | 3/2011 | Swanson et al. | |
| 2011/0130803 A1* | 6/2011 | McDonald | A61N 1/0534 607/45 |
| 2011/0270330 A1* | 11/2011 | Janzig | A61N 1/3752 607/2 |
| 2012/0123318 A1 | 5/2012 | Ek et al. | |
| 2012/0296405 A1 | 11/2012 | Thenuwara et al. | |

OTHER PUBLICATIONS

International Preliminary Report on Patentability from International Application No. PCT/US2014/028523, dated Sep. 24, 2015, 6 pp.
U.S. Appl. No. 14/206,650, by Alan Shi, filed Mar. 12, 2014.
International Search Report and Written Opinion from counterpart International Application No. PCT/US2014/028523, dated Jun. 18, 2014, 8 pp.
Office Action from U.S. Appl. No. 14/206,650, dated Jul. 8, 2015, 11 pp.
Final Office Action from U.S. Appl. No. 14/206,650, dated May 16, 2016, 11 pp.
Response to Final Office Action filed Jul. 21, 2016, from U.S. Appl. No. 14/206,650, 10 pp.
Advisory Action dated Aug. 19, 2016, from U.S. Appl. No. 14/206,650, 3 pp.
Notice of Appeal from U.S. Appl. No. 14/206,650, 1 pp.
Pre-Appeal Brief Request for Review from U.S. Appl. No. 14/206,650, 6 pp.
Communication pursuant to Article 94(3) EPC from counterpart European Application No. 14717621.8, dated Nov. 11, 2016, 6 pp.
Response to Office Action dated Mar. 9, 2017 from U.S. Appl. No. 14/206,650, filed Jun. 9, 2017, 8 pp.
Response to Communication pursuant to Article 94(3) EPC dated Nov. 11, 2016, from counterpart European Application No. 14717621.8, filed May 18, 2017, 18 pp.
Office Action from U.S. Appl. No. 14/206,650, dated Mar. 9, 2017, 11 pp.
Final Office Action from U.S. Appl. No. 14/206,650, dated Jun. 29, 2017, 12 pp.
Response to Office Action dated Sep. 29, 2017, from U.S. Appl. No. 14/206,650, filed Aug. 29, 2017, 10 pp.
Notice of Appeal for U.S. Appl. No. 14/206,650, filed Oct. 2, 2017, 2 pp.
Pre-Appeal Brief Request for Review for U.S. Appl. No. 14/206,650, filed Oct. 2, 2017, 6 pp.
Advisory Action from U.S. Appl. No. 14/206,650, dated Oct. 2, 2017, 3 pp.
Examination Report from counterpart European Application No. 14717621.8, dated Mar. 2, 2018, 3 pp.
Examiner's Answer from U.S. Appl. No. 14/206,650, dated Mar. 22, 2018, 11 pp.
Reply Brief from co-pending U.S. Appl. No. 14/206,650, filed May 22, 2018, 8 pp.
Response to Examination Report dated Mar. 2, 2018, from counterpart European Application No. 14717621.8 filed Jun. 11, 2018, 8 pp.
Notice of Allowance from U.S. Appl. No. 14/206,650, dated Apr. 29, 2019, 7 pp.
Decision on Appeal from U.S. Appl. No. 14/206,650, dated Jan. 31, 2019, 7 pp.

* cited by examiner

MEDICAL LEADS AND TECHNIQUES FOR MANUFACTURING THE SAME

This application claims the benefit of U.S. Provisional Application No. 61/798,355, filed on Mar. 15, 2013, the entire content of which is incorporated herein by reference.

TECHNICAL FIELD

The present disclosure relates to medical devices, more particularly to medical device leads and electrodes configured for delivery of electrical stimulation therapy and/or sensing of electrical signals.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

SUMMARY

Some examples of the present disclosure relate to medical device leads including one or more electrodes for use in medical device systems. The medical device leads may include one or more electrodes each formed of two or more materials having different compositions. For example, the composition of a first portion of the electrode may be formed of a material that allows for the electrode to be mechanically and electrically coupled to a lead wire within the lead body via welding, while a second portion of the electrode is formed of another material that defines an outer surface of the electrode for the transmission of electrical signals across the interface. The first portion may be mechanically and electrically coupled to the second portion of the electrode via a technique other than that of welding, e.g., because the dissimilar compositions of the first and second portion do not allow for suitable welding of the portions to each other.

In one example, the disclosure relates to a medical device comprising a lead including an electrically conductive lead wire; and an electrode electrically coupled to the lead wire, the electrode including a first portion and a second portion, wherein the first portion defines an exposed outer surface of the electrode and is bonded to the second portion along a first interface, wherein the second portion is electrically and mechanically coupled to the lead wire along a second interface different from the first interface via laser welding to couple the lead wire to the electrode, wherein an electrical signal may be transferred between the lead wire and exposed outer surface of the first portion via the second portion, and wherein the first portion is formed from a first material having a first composition, and the second portion is formed from a second material having a second composition different from the first composition.

In another example, the disclosure relates to a method for forming a medical device lead, the method comprising bonding a first portion of an electrode to a second portion of the electrode along a first interface, wherein the first portion defines an exposed outer surface of the electrode, wherein the first portion is formed from a first material having a first composition, and the second portion is formed from a second material having a second composition different from the first composition; and welding the second portion to an electrically conductive lead wire of a lead to electrically and mechanically coupled to the lead wire and the second portion along a second interface different from the first interface, wherein an electrical signal may be transferred between the lead wire and exposed outer surface of the first portion via the second portion.

The details of one or more aspects of the disclosure are set forth in the accompanying drawings and the description below. Other features, objects, and advantages will be apparent from the description and drawings, and from the claims.

DETAILED DESCRIPTION

Figure 1:
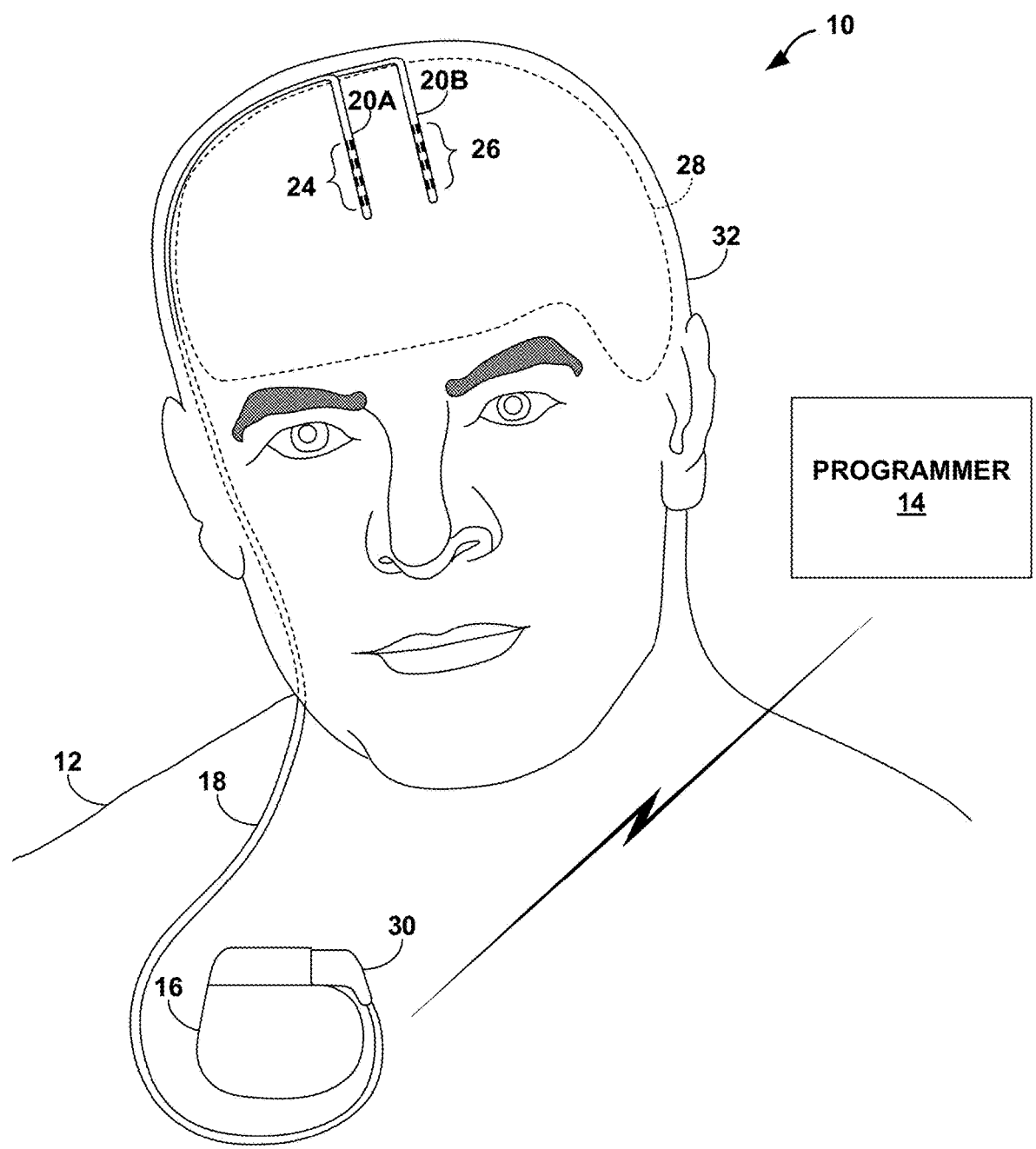
FIG. 1 is a conceptual diagram illustrating an example medical device system.

As described above, some examples of the disclosure relate to medical device leads (also referred to as "medical leads" or "leads") including one or more electrode. Using the lead and electrode, a medical device may deliver and/or sense electrical signals to provide therapy to a patient to treat a patient condition. Medical leads may include a conductive electrode member electrically and mechanically connected to one or more conductive lead wires extending through the lead body. Electrical stimulation from a medical device may be conductive along the lead wire to be delivered across the electrode surface.

With requirements to be able to steer stimulation field, segmented electrodes have been employed. Segmented electrodes, which are electrodes that do not extend around the full circumference of the lead body at the point of stimulation (e.g., may extend anywhere from about 1 degree of arc to about 359 degrees of arc), may be desired for targeted stimulation or for efficient use of energy.

In some examples, the electrode and lead wires of a medical lead may each be formed of materials having substantially the same or similar composition. For example, one lead design includes one or more platinum iridium electrodes mounted on the distal ends of a platinum-iridium (Pt—Ir) lead wire. Each of the electrodes may be electrically and mechanically coupled to the Pt—Ir lead wire via lasing welding. However, to reduce heating during MRI scanning it is sometimes preferred to use conductors with higher electrical resistivity than platinum-iridium alloys. In some instances, conductor materials such as beta titanium alloys (e.g., Ti-15% Mo) which have higher electrical resistivity may be used. Such metals may not be desirable for the portion of the electrode in direct contact with the body tissue being stimulated. This is because titanium and many of the titanium allows cannot be used at electrical stimulation charge densities as high as platinum or platinum-iridium alloys safely permit. Further, Ti and Ti alloys, and Ti-15Mo alloys in particular, may exhibit superior fatigue life, e.g., as compared to that of Pt or Pt—Ir lead wires.

While providing for MRI compatibility in a medical lead, welding dissimilar metals such as Pt—Ir and titanium alloys can be difficult. For example, micro cracking may occur in an intermetallic layer when a titanium alloy and Pt—Ir are welded together, which may impose a reliability concern. The micro cracking may negatively influence the integrity of a medical lead due to the segmented electrode pulling away from the lead body, in some cases resulting in an inoperative lead.

In accordance with examples of the disclosure, medical lead designs including an electrode with two (or more) portions have different metal compositions are described. Such example designs may be referred to in some examples as "bi-metal electrode" or "multi-metal electrode" designs, and may be employed in segmented electrode configurations. In some examples, the electrode may include a first portion formed of a metal composition that allows for suitable welding to a lead wire. For example, the first portion of the electrode may have a composition that is the same or substantially similar to that of the lead wire. A second portion of the electrode may define the outer surface of the electrode and have a different composition from that of the first portion and the lead wire. For example, the composition of the second portion may be desirable for delivering electrical stimulation to tissue of a patient but may not be suitable to be mechanically coupled directly to the lead wire via welding. Instead, the first portion may be mechanically coupled directly to the second portion across an interface formed using a technique other than that of welding. In this manner, the second portion of the electrode defining the outer stimulation surface of the electrode may be mechanically and electrically coupled to the lead wire via the first portion of the electrode. In some examples, the first portion and lead wire may be formed of titanium or titanium alloys while the second portion of the electrode may be formed of Pt—Ir.

Example bi-metal designs in medical leads may allow for one or more advantages. In some examples, a bi-metal electrode design enables electrodes such as segmented electrodes to be employed but may reduce lead integrity concerns associated with micro cracking. Moreover, some examples of this disclosure may reduce or substantially eliminate the bump associated with welding dissimilar metals to reduce concerns associated with tissue damage during removal of the medical lead from a patient.

FIG. 1 is a conceptual diagram illustrating an example stimulation system 10 with stimulation lead 20 implanted in the brain of a patient 10. For ease of illustration, examples of the disclosure will primarily be described with regard to implantable electrical stimulation leads and implantable medical devices that neurostimulation therapy to a patient's brain in the form of deep brain stimulation (DBS), the features and techniques described herein may be useful in other types of medical device systems, which may include other types of implantable medical leads for use with medical devices, such as, e.g., implantable medical devices (IMDs). For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient.

Therapy system 10 includes medical device programmer 14, IMD 16, lead extension 18, and one or more leads 20A and 20B (collectively "leads 20") with respective sets of electrodes 24, 26. IMD 16 includes a stimulation therapy module that includes an electrical stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to as a DBS system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28).

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing to substantially enclose components, such as a processor, therapy module, and memory.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Although FIG. 1 illustrates system 10 as including two leads 20A and 20B coupled to IMD 16 via lead extension 18, in some examples, system 10 may include one lead or more than two leads.

Leads 20 may deliver electrical stimulation via electrodes 24, 26 to treat any number of neurological disorders or diseases in addition to movement disorders, such as seizure disorders or psychiatric disorders. Leads 20 may be implanted within a desired location of brain 28 via any suitable technique, such as through respective burr holes in a skull of patient 12 or through a common burr hole in the cranium 32. Leads 20 may be placed at any location within brain 28 such that electrodes 24, 26 of leads 20 are capable of providing electrical stimulation to targeted tissue during treatment. In the examples shown in FIG. 1, electrodes 24, 26 of leads 20 are shown as segmented electrodes. In other examples, electrodes 24, 26 of leads 20 may have different configurations including ring or paddle electrodes. Electrodes 24, 26 of leads 20 may have a complex electrode array geometry that is capable of producing shaped electrical fields. In this manner, electrical stimulation may be directed to a specific direction from leads 20 to enhance therapy efficacy and reduce possible adverse side effects from stimulating a large volume of tissue.

In accordance with one or more examples of the disclosure, electrodes 24 and 26 may have a "bi-metal" or "multi-metal" configuration as electrodes 24 and 26 may include two (or more) portions having different metal compositions. As noted above, in some examples, each of electrodes 24, 26 may include a first portion formed of a metal composition that allows for suitable welding to a lead wire. For example, the first portion of electrode 24 may have a composition that is the same or substantially similar to that of the lead wire (not shown) extending through lead 20. A second portion of electrode 24 may define the outer surface of the electrode and have a different composition from that of the first portion and the lead wire. For example, the composition of the second portion may be desirable for delivering electrical stimulation to tissue of a patient but may not be suitable to be mechanically coupled directly to the lead wire via welding. Instead, the first portion may be mechanically coupled directly to the second portion across an interface formed using a technique other than that of laser welding. The second portion of the electrode defining the outer stimulation surface of the electrode may be mechanically and electrically coupled to the lead wire via the first portion of the electrode IMD 16 may deliver electrical stimulation therapy to brain 28 of patient 12 according to one or more stimulation therapy programs. A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 24, 26 are conducted to the sensing module within IMD 16 via conductors within the respective lead 20A, 20B. As described in further detail below, in some examples, a processor of IMD 16 may sense the bioelectrical signals within brain 28 of patient 12 and controls delivery of electrical stimulation therapy to brain 28 via electrodes 24, 26.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14.

Figure 2:
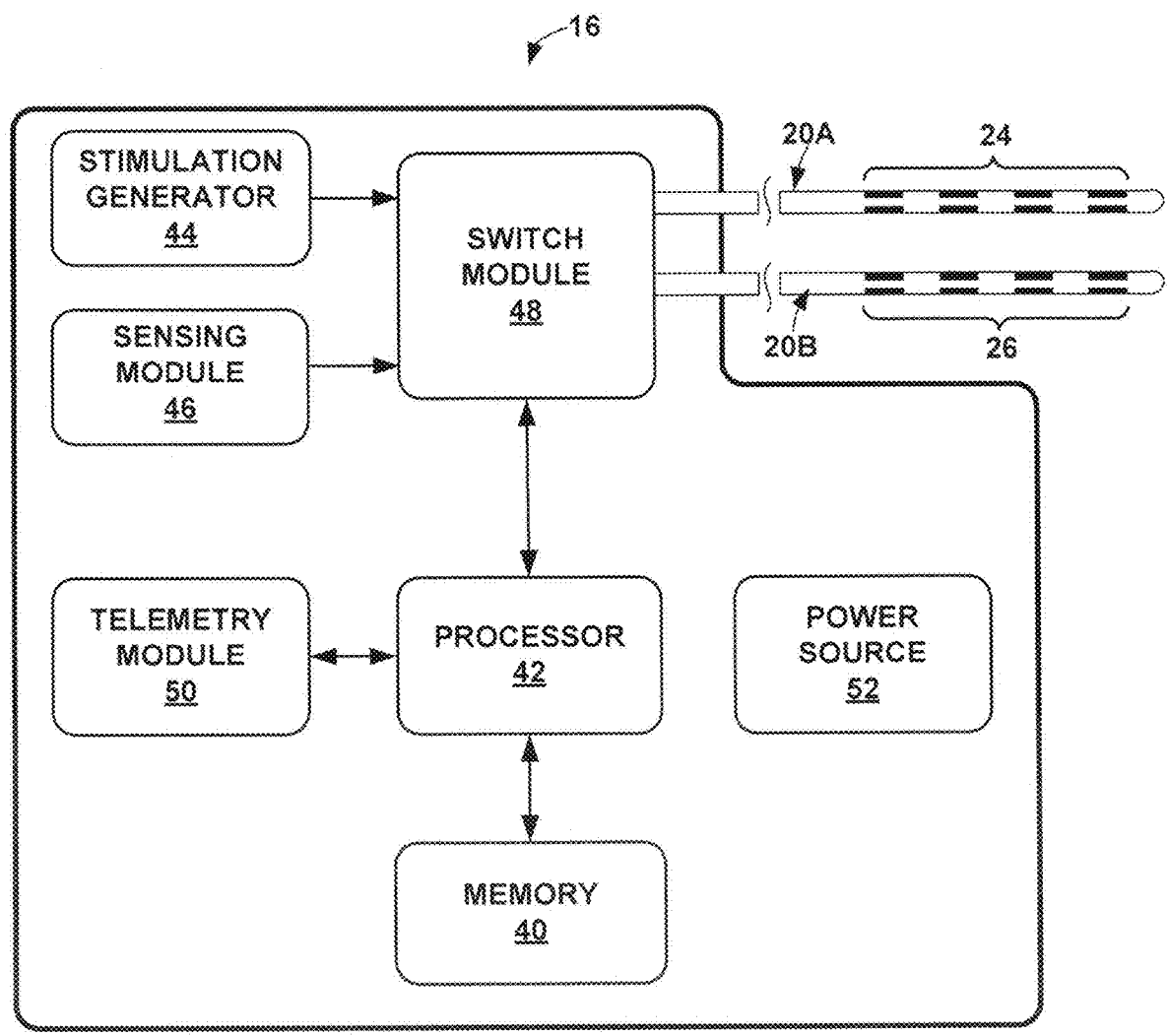
FIG. 2 is a conceptual diagram illustrating an example implantable medical device.

FIG. 2 is a functional block diagram illustrating components of IMD 16. In the example shown in FIG. 2, IMD 16 includes memory 40, processor 42, stimulation generator 44, sensing module 46, switch module 48, telemetry module 50, and power source 52. Processor 42 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

In the example shown in FIG. 2, sensing module 46 senses bioelectrical brain signals of patient 12 via select combinations of electrodes 24, 26. The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 24, 26 in order to remove undesirable artifacts from the signal, such as noise from cardiac signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In some examples, sensing module 46 may sense brain signals substantially at the same time that IMD 16 delivers therapy to patient 14. In other examples, sensing module 46 may sense brain signals and IMD 16 may deliver therapy at different times.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. Memory 40 may be considered, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, processor 42 controls switch module 48 to sense bioelectrical brain signals with selected combinations of electrodes 24, 26. In particular, switch module 48 may create or cut off electrical connections between sensing module 46 and selected electrodes 24, 26 in order to selectively sense bioelectrical brain signals, e.g., in particular portions of brain 28 of patient 12. Processor 42 may also control switch module 48 to apply stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 22A, 22B and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. In some examples, IMD 16 may include separate current sources and sinks for each individual electrode (e.g., instead of a single stimulation generator) such that switch module 48 may not be necessary.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Telemetry module 50 may support wireless communication between IMD 16 and an external programmer 14 or another computing device under the control of processor 42. Telemetry module 50 in IMD 16, as well as telemetry modules in other devices and systems described herein, such as programmer 14, may accomplish communication by radiofrequency (RF) communication techniques. In addition, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
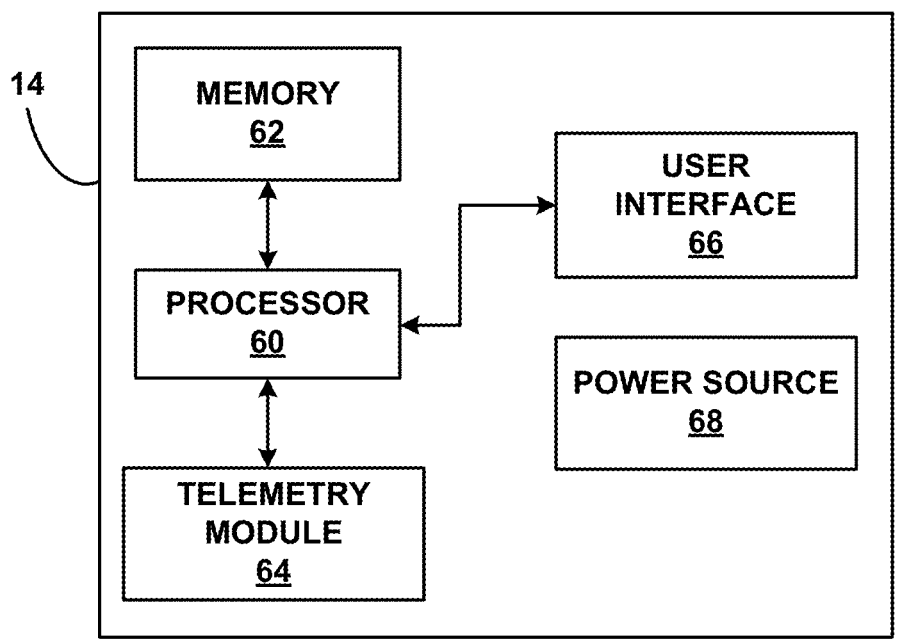
FIG. 3 is a conceptual diagram illustrating an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

Memory 62 may include instructions for operating user interface 66 and telemetry module 64, and for managing power source 68. Memory 62 may also store any therapy data retrieved from IMD 16 during the course of therapy. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14. Power source 68 may include a battery and a power generation circuit to produce the operating power. In some examples, the battery may be rechargeable to allow extended operation.

Figure 4A:
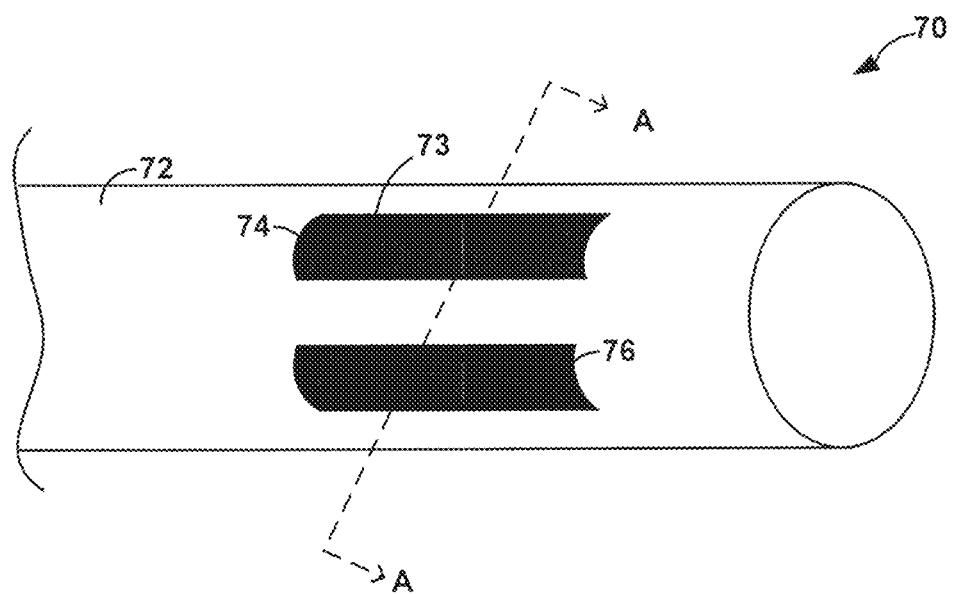
FIGS. 4A and 4B are schematic diagrams illustrating an example medical lead for use in a medical device system.
Figure 4B:
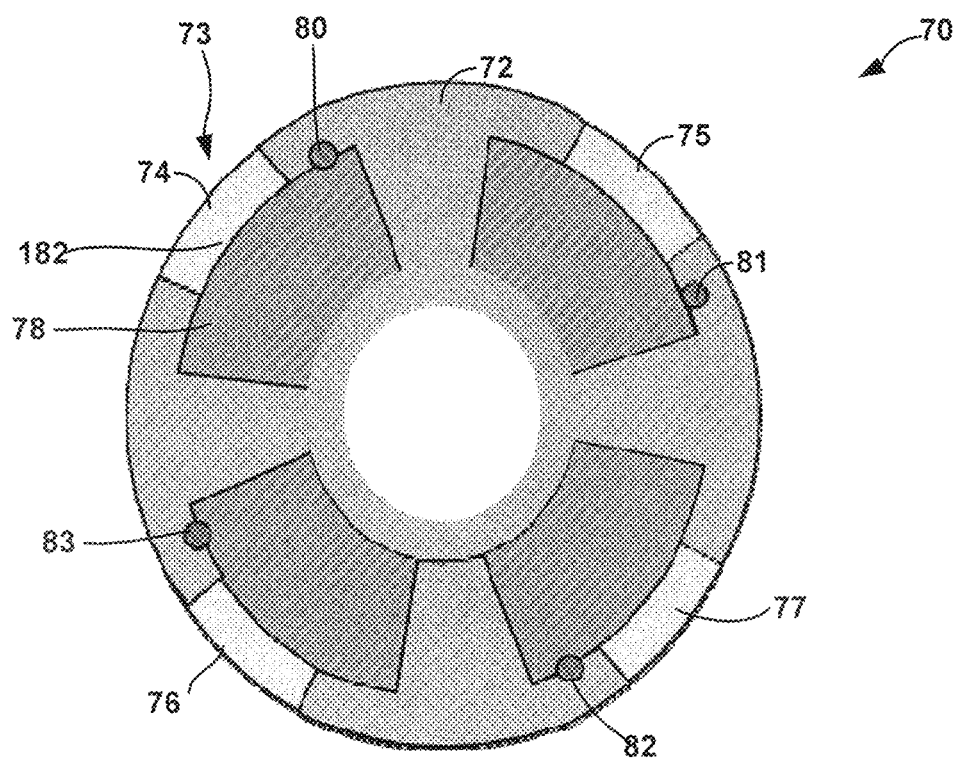

FIGS. 4A and 4B are schematic diagram illustrating an example medical lead 70 for use in a medical device system, such as, e.g., medical device system 10 of FIG. 1. FIG. 4A is a perspective view of lead 70 and FIG. 4B is a cross-sectional view of lead 70 taken along line A-A. Lead 70 may be substantially the same or similar to that of lead 20A or 20B of FIG. 1. Four ease of description, lead 70 will be described with regard to system 10 of FIG. 1. As shown, lead 70 includes four segmented electrodes (only electrode 73 is labeled for clarity) with outer surface portion 74-77 exposed on lead body 72. Lead body 72 is formed of an electrically insulating, biocompatible material that separates the four electrodes from each other. Example materials for lead body 72 include polyurethanes, polysulfone, and/or polyether ether ketone (PEEK). Lead body 72 also includes lead wires 80-83 which run the length of lead body 72 and electrically couple the four segmented electrodes to IMD 16.

Each of the four electrodes in FIGS. 4A and 4B are electrodes having a "bi-metal" or "multi-metal" design. For example, as shown in FIG. 4B, electrode 73 includes both outer surface portion 74 and inner portion 78. Outer portion 74 is mechanically and electrically coupled to inner portion 78 along interface 182. Inner portion 78 may be electrically and mechanically coupled to conductive lead wire 80 via a weld such as a laser weld. However, lead wire 80 is not in direct contract or directly bonded to outer portion 74. Instead, to deliver electrical stimulation via electrode 73, the electrical stimulation may be conducted from lead wire 80 out of the exposed surface of outer portion 74 by way of conduction through inner portion 78. Similarly, lead wire 80 may be mechanically coupled to outer portion 74 via inner portion 78.

Outer surface portion 74 is formed of a material with a composition different than that of the material which forms inner portion 78. The compositions of outer surface portion 74 and inner portion 78 may be such that it is undesirable or impractical to mechanically couple the portions together via welding, such as, e.g., laser welding. Accordingly, inner portion 78 and outer portion 74 are mechanically coupled at interface 182 via some bond other than that of a weld. As will be described further, in some examples, inner portion 78 and outer portion 74 may be mechanically coupled via non-laser welding processes including, e.g., diffusion bonding, rolling, drawing, co-extrusion, hot isostatic pressing, electron magnetic pulse welding, plating and the like In some examples, inner portion 78 and outer portion 74 may be mechanically coupled via diffusion bonding. Diffusion bonding may also be referred to as diffusion welding or "sintering." A diffusion-bond may be formed between tangent metal surfaces when enough atoms or molecules migrate across the interface between the metals to create new metallurgical grains bridging the gap. In some examples, this process occurs at elevated temperatures and/or pressures. One example of diffusion bonding is when two metals part stick to each other during heat treatment without the addition of any braze alloy or bonding agent.

Outer portion 74 may be formed of a composition suitable for forming the outer surface of an electrode. For example, outer portion 74 may be formed of Pt and alloys thereof. As noted above, Pt—Ir may be a preferred material for forming an electrode surface that is in contact with body tissue because of the high charge density levels that these materials can safely accommodate and is used as electrode material in approved deep brain stimulation leads. Additionally, platinum and platinum-iridium alloys are biocompatible and biostable. In some examples, the composition of outer portion 24 may include one or more additives, elements, or compounds other than Pt—Ir. In one example, outer portion 74 may consist essentially of Pt—Ir, where any additionally material in present only in an amount that does not alter one or more properties of the material in a manner that does not allow outer portion 74 to function as described herein.

Conversely, lead wire 80 may be formed of a composition that provides reduced heating during MRI scanning, e. g., as compared to that of Pt—Ir. For example, lead wire 80 may be formed of conductor materials such as titanium, titanium alloys, such as, e.g., Ti-15Mo, or other low modulus beta titanium alloys, which have high resistance to reduce MRI induced heating, may be used to form a lead wire. In some examples, lead wire 80 may exhibit a wire resistivity of greater than approximately 80 $\mu\Omega$-cm.

Example alloying elements for lead wire 80 may include Mo, Nb, Ta, Zr, Fe, Sn, Fe and Al and combinations thereof. In one example, lead wire 80 may be formed of tantalum, niobium, or alloys thereof. Example alloys may include, for example, Ti-15Mo, Ti-15Mo-5Zr, Ti-29Nb-13Ta-5Zr, Ti-15Mo-3Zr-3Al. In one example, lead wire 80 may consist essentially of titanium or titanium alloy, where any additionally material in present only in an amount that does not alter one or more properties of the material in a manner that does not allow lead wire 80 to function as described herein. In some examples, lead wire 80 may have a diameter between approximately 2.5 mils to approximately 5 mils.

In some cases, including those noted above, it may be desirable to weld, e.g., laser weld, a Pt—Ir electrode directly to a lead wire formed of titanium or titanium alloys. Thus, inner portion 78 of electrode 73 may be formed of a composition suitable for conducting electrical signals from lead wire 80 to outer portion 74 as well as being capable of being welded, e.g., laser welded, to lead wire 80 as described herein. For example, inner portion 78 may be formed of titanium and alloys thereof, such as, e.g., Ti15Mo. Example alloying elements may include Mo, Nb, Ta, Zr, Fe, Sn, Fe and Al and combinations thereof. Example titanium compositions include commercially pure titanium grade 1, 2, 3, and 4. In some examples, alloying elements, such as, e.g., Mo, may be present between about 5 to about 25 wt %. In one example, inner portion 78 may be formed of tantalum, niobium, or alloys thereof.

In some examples, inner portion 78 may have substantially the same composition of that of lead wire 80. In other examples, inner portion 78 may have a different composition that that of lead wire 80 but the compositions are such that lead wire 80 may be suitably welded to inner portion 78. For example, lead wire 80 may be formed of tantalum while inner portion 78 may be formed of titanium, or vice versa. In some examples, the composition of inner portion 78 may include one or more additives, elements, or compounds other than Ti or Mo. In one example, inner portion 78 may consist essentially of Ti or TiMo, where any additionally material in present only in an amount that does not alter one or more properties of the material in a manner that does not allow inner portion 78 to function as described herein.

Based on the composition of inner portion 78 and outer portion 74, electrode 73, lead 70 may be described as a bi-metal or multi-metal electrode. The design configuration of electrode 73 allows for lead 70 to include lead wire 80 to be formed of a composition that provides reduced MRI induced heating, e. g., as compared to that of Pt—Ir, while also allowing for outer surface portion 74 to be formed of a composition with properties desirable for delivery and/or sensing of electrical signals. Although only the configuration and design of electrode 73 has been described, each of the other electrodes of lead 70 may have the same or substantially similar configuration and design as that of electrode 73.

FIGS. 5A-5D are schematic diagrams illustrating example medical device lead at various stages during manufacture. Such a manufacturing process may be used to form an example lead having a configuration the same or substantially similar to that of lead 70. For ease of description, features in FIGS. 5A-5D generally corresponding to similar features of lead 70 are similarly numbered.

Figure 5A:
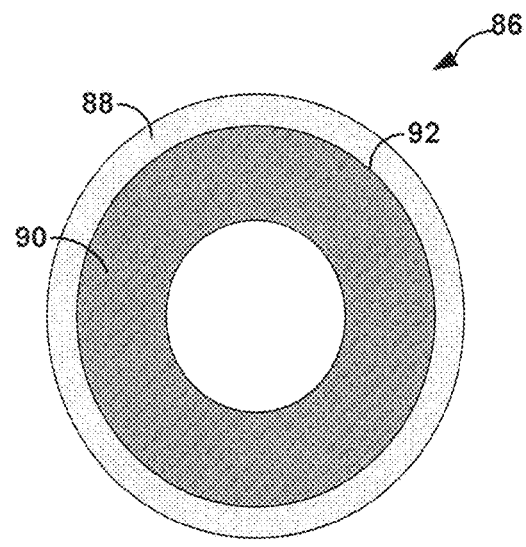
FIGS. 5A-5D are schematic diagrams illustrating an example medical device lead at various stages during manufacture according to one example lead configuration.

As shown in FIG. 5A, electrode preform 86 may be a substantially tubular structure having outer layer 88 and inner layer 90. Outer layer 88 may have a composition that is the same or similar to that described for outer surface portion 74 of electrode 73. Inner layer 90 may have a composition that is the same or similar to that described for inner portion 78 of electrode 73. As it may be undesirable to laser weld inner layer 90 to outer layer 88 via a laser weld, inner layer 90 and outer layer 88 may be mechanically coupled at interface 92 via some bond other than that of a laser weld. In some examples, inner layer 90 and outer layer 88 may be mechanically coupled via non-laser welding processes including, e.g., diffusion bonding, rolling, drawing, co-extrusion, hot isostatic pressing, electron magnetic pulse welding, plating and the like. In one example, the portions of the two tubes of dissimilar metals may be bonded together via electromagnetic pulse technology (EMPT).

Figure 5B:
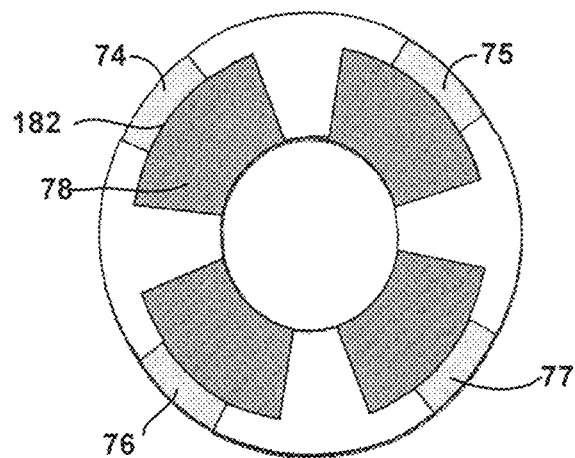

As shown in FIG. 5B, using one or more suitable techniques, portions of both inner layer 90 and outer layer 88 of electrode preform 86 may be removed, e.g., using partial machining techniques. The resulting configuration generally corresponds to that of lead 70 without lead body 72 and four lead wire 80-83 shown in FIG. 4B.

Figure 5C:
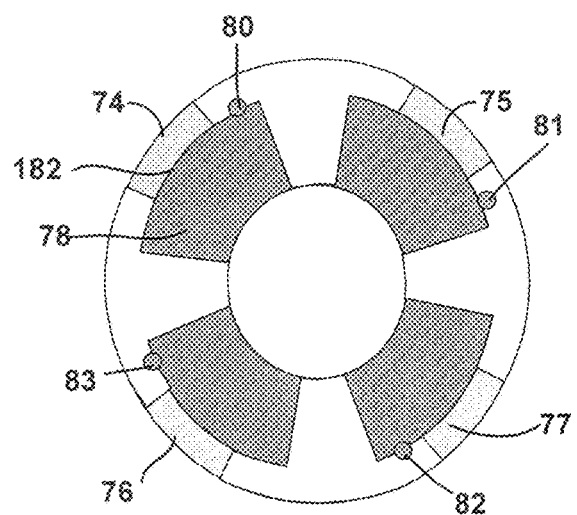

As shown in FIG. 5C, lead wires 80-83 are welded, e.g., laser welded, to corresponding surfaces of inner portions in accordance with the configuration of lead 70 without lead body 72 shown in FIG. 4B. For example, lead wire 80 may be bonded to inner portion 78 of electrode 73.

Figure 5D:
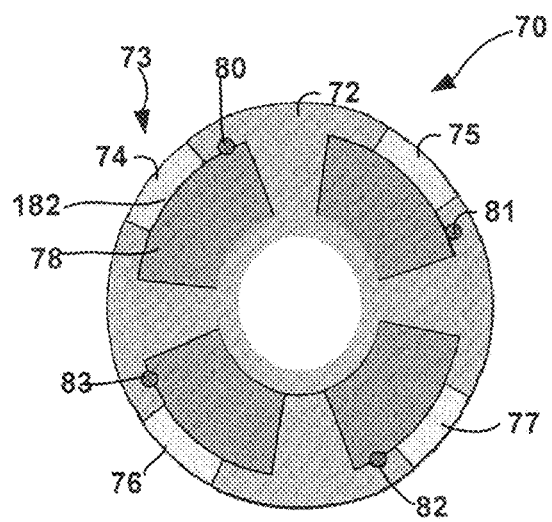

As shown in FIG. 5D, once the welding is complete, the void areas or cavities separating the conductive materials may be refilled with an electrically insulating, biocompatible material to form lead body 72 and electrically isolate the resulting four electrodes from each other. Once refilled, the configuration illustrated in FIG. 5D is the same or substantially similar to that of lead 70 shown in FIG. 4B.

Figure 6A:
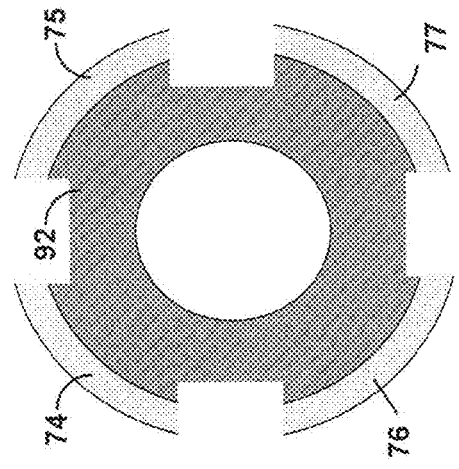
FIGS. 6A-6D are schematic diagrams illustrating an example medical device lead at various stages during manufacture according to another example lead configuration.
Figure 6B:
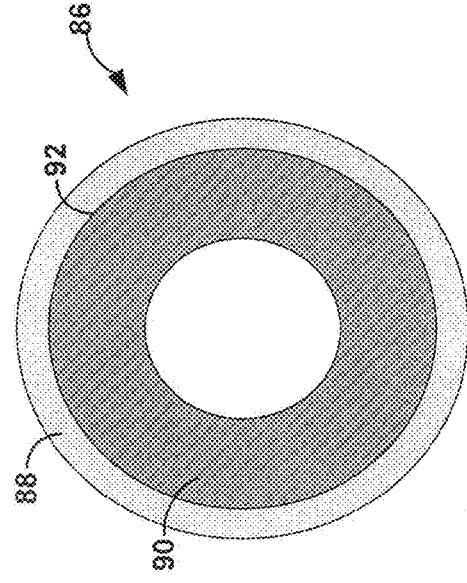
Figure 6C:
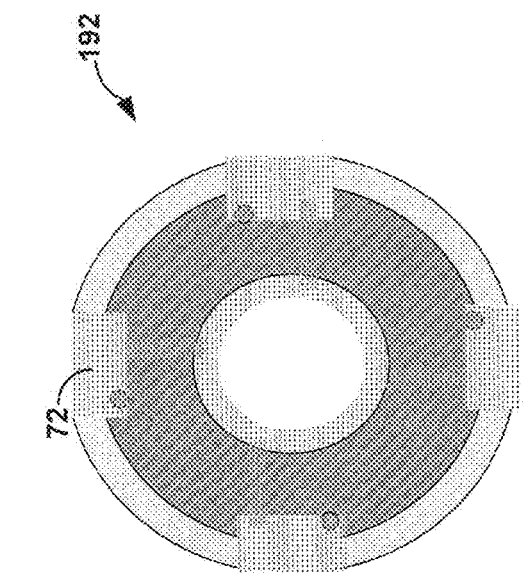
Figure 6D:
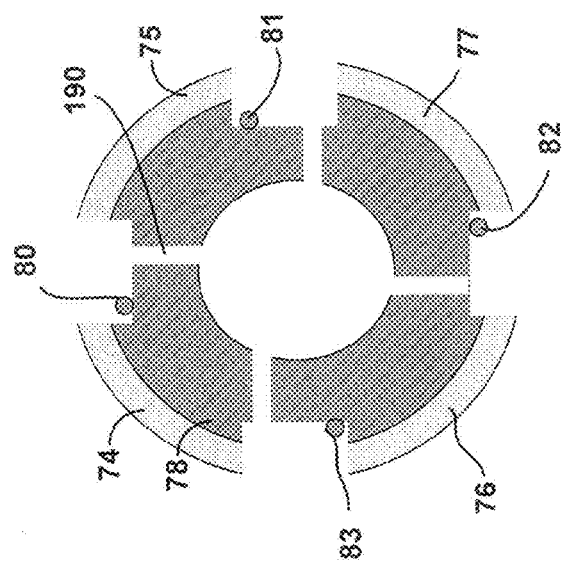

FIGS. 6A-6D are schematic diagrams illustrating another example medical device lead at various stages during manufacture. The configuration of the resulting medical device lead shown in FIG. 6D is similar to that of lead 7 of FIG. 4B, and like features are similarly numbered. For example, the resulting configuration includes four segmented electrodes. Electrode preform 86 of FIG. 6A may be the same are substantially similar to that described with regard to FIG. 5A. As shown in FIG. 6B, using one or more suitable techniques, portions of both inner layer 90 and outer layer 88 of electrode preform 86 may be removed. However, the resulting void areas or cavities to not extend all the way through inner portion 90.

As shown in FIG. 6C, lead wires 80-83 are welded to corresponding surfaces of inner portions in accordance with the configuration of lead 70 without lead body 72 shown in FIG. 4B. For example, lead wire 80 may be bonded to inner portion 78 of electrode 73. Additional portions of inner portion 78 are removed to form a channel (such as channel 190) extend through inner portion 90 for each of the electrodes. As shown in FIG. 6D, similar to that of FIG. 5D the void areas and channels separating the conductive materials may be refilled with an electrically insulating, biocompatible material to form lead body 192 and electrically isolate the resulting four electrodes from each other.

Figure 9B:
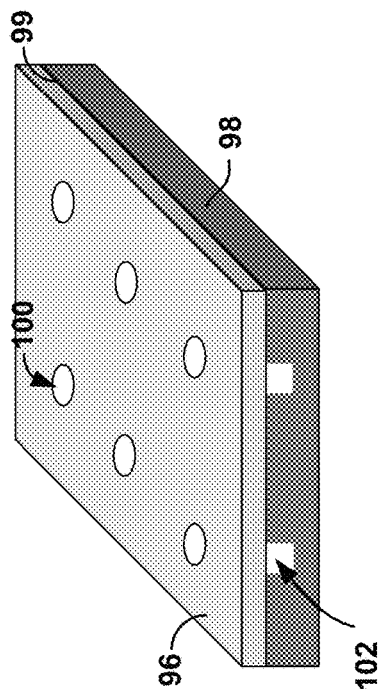
FIGS. 9A-9D are schematic diagrams illustrating an example medical device lead at various stages during manufacture according to another example lead configuration.
Figure 9D:
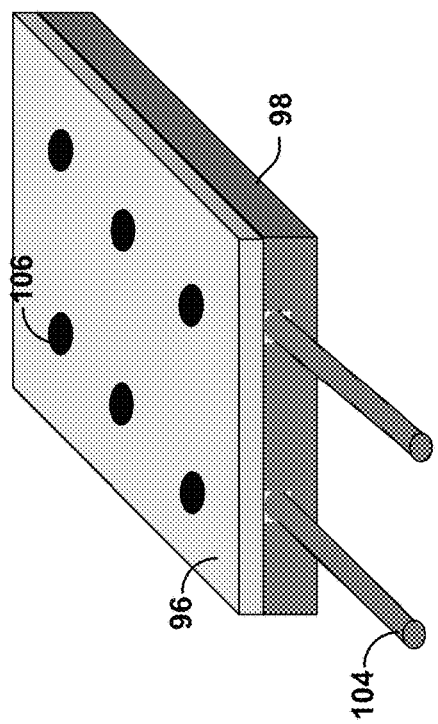
Figure 9A:
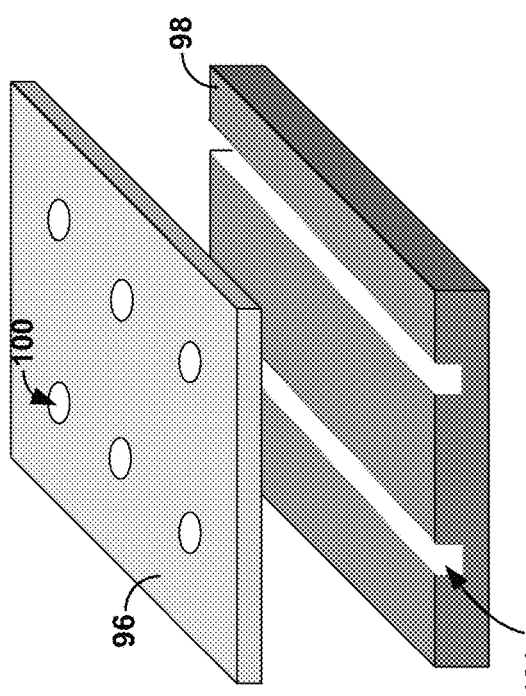

FIGS. 9A-9D are schematic diagrams illustrating an example electrode and lead wire at various stages during manufacture according to another example electrode configuration. Unlike that of the electrodes and leads previously described, the technique illustrated in FIGS. 9A-9D may be used to form electrodes having two or more portions of a different composition using a non-tubular preform. As shown in FIGS. 9A and 9B, first portion 96 and second portion 98 may be bonded to each other across interface 99. First portion 96 may be a substantially planar substrate including one or more apertures, such as, aperture 100, extending through first portion 96. Second portion 98 also defines a substantially planar substrate that includes one or more channels, such as, channel 102, which extend partially into the surface of second portion 98. When bonded to each other, the apertures in first portion 96 may align with the channels in second portion 98.

First portion 96 and second portion 98 are formed of different compositions. In particular, first portion 96 may have a composition that is the same or substantially similar to that described for the composition of outer portion 74 of electrode 73 in FIGS. 4A and 4B. When incorporated into a lead, the surface of first portion 96 may form the outer surface of an electrode. Conversely, second portion 98 may have a composition that is the same or substantially similar to that described for the composition of inner portion 78 of electrode 73 in FIGS. 4A and 4B. Second portion 98 may be coupled to a lead wire, such as, lead wire 104, via laser welding.

Figure 9C:
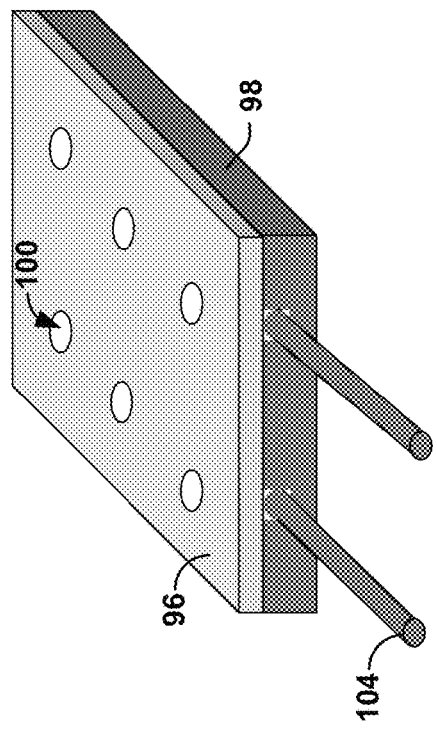

Similar to that of outer portion 74 and inner portion 78 of electrode 73, first portion 96 and second portion 98 may be mechanically coupled to each other across interface 99 using a technique other than that of laser welding, including, e.g., diffusion bonding, rolling, drawing, co-extrusion, hot isostatic pressing, electron magnetic pulse welding, plating and the like. Once mechanically coupled to each other, a lead wire may be inserted into the channels formed in second portion 98. For example, as illustrated in FIG. 9C, lead wire 104 may be inserted into channel 102 of second portion 98. Lead wire 104 may have a composition substantially similar to that of lead wire 80 shown in FIG. 4B, for example. When inserted in channel 102, lead wire 104 may be welded to second portion 98 through the apertures, such as, aperture 100, formed through first portion 108. Once welded to each other, the void space in the channels and apertures may be refilled with an electrically insulating, biocompatible material, such as, e.g., material 106, shown in FIG. 9D.

The technique of FIGS. 9A-9D may be used to form only a single electrode or multiple electrodes at once. For example, once assembled as shown in FIG. 9D, electrode assembly 108 may be separated, e.g., along the midline, to form two electrodes corresponding to the two leads wires shown in FIG. 9D. Depending on the number of channels formed in second portion 98 and apertures in first portion 96, first portion 96 and second portion 98 may be manufactured into a single assembly that may be divided into a plurality of electrodes rather than requiring each electrode individually.

Figure 10A:
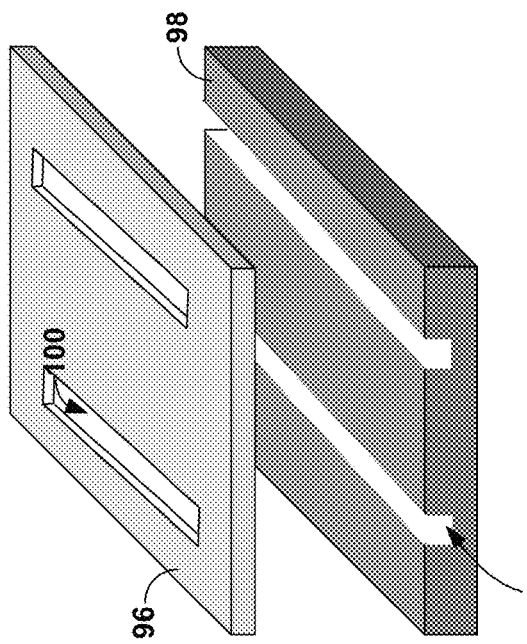
FIGS. 10A-10D are schematic diagrams illustrating an example medical device lead at various stages during manufacture according to another example lead configuration.
Figure 10B:
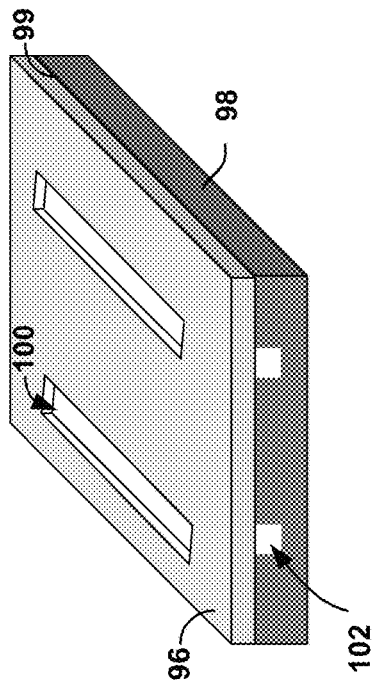
Figure 10C:
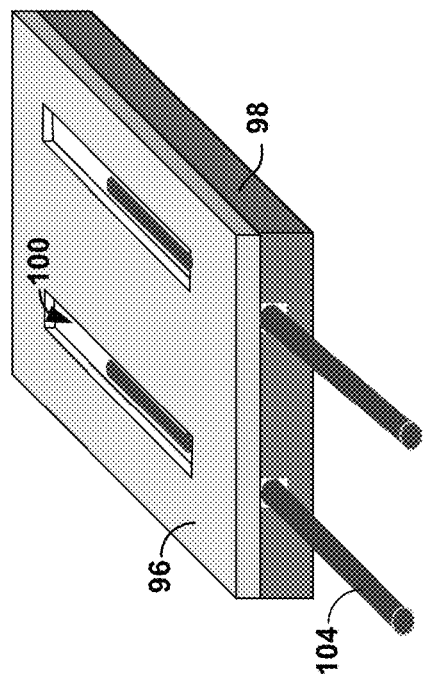
Figure 10D:
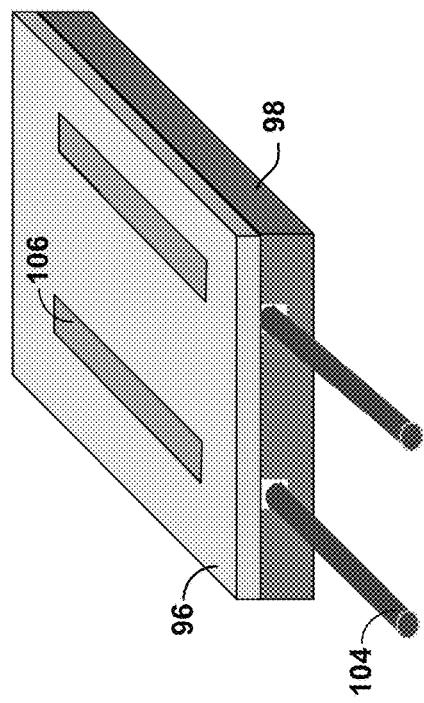

FIGS. 10A-10D are schematic diagrams illustrating an example electrode and lead wire at various stages during manufacture according to another example electrode configuration. The technique used to assemble first portion 96 and second portion 98 is the same or substantially similar to that of FIGS. 9A-9D. However, as shown in FIG. 10A-10D, first portion 96 includes only a single aperture or slot, such as, e.g., aperture 100, for laser welding each lead wire in a channel, such as, e.g., lead wire 104 in channel 102. Once assembled as shown in FIG. 10D, electrode assembly 108 may be separated to form two electrodes corresponding to the two lead wires.

Figure 7:
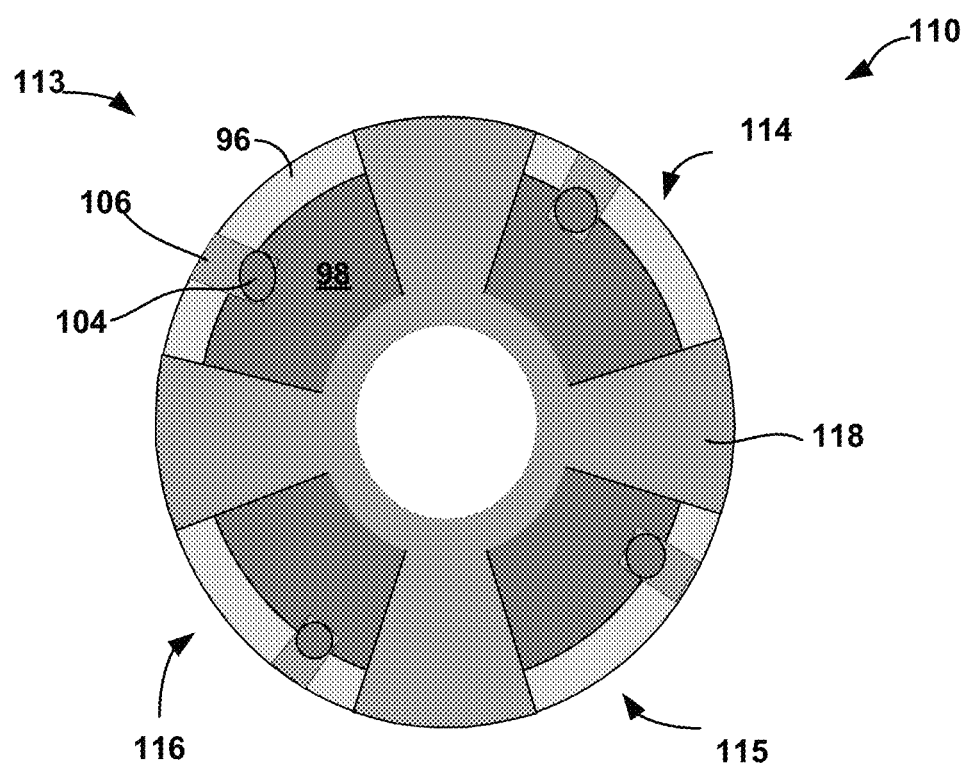
FIGS. 7 and 8 are schematic diagrams illustrating another example medical lead for use in a medical device system.
Figure 8:
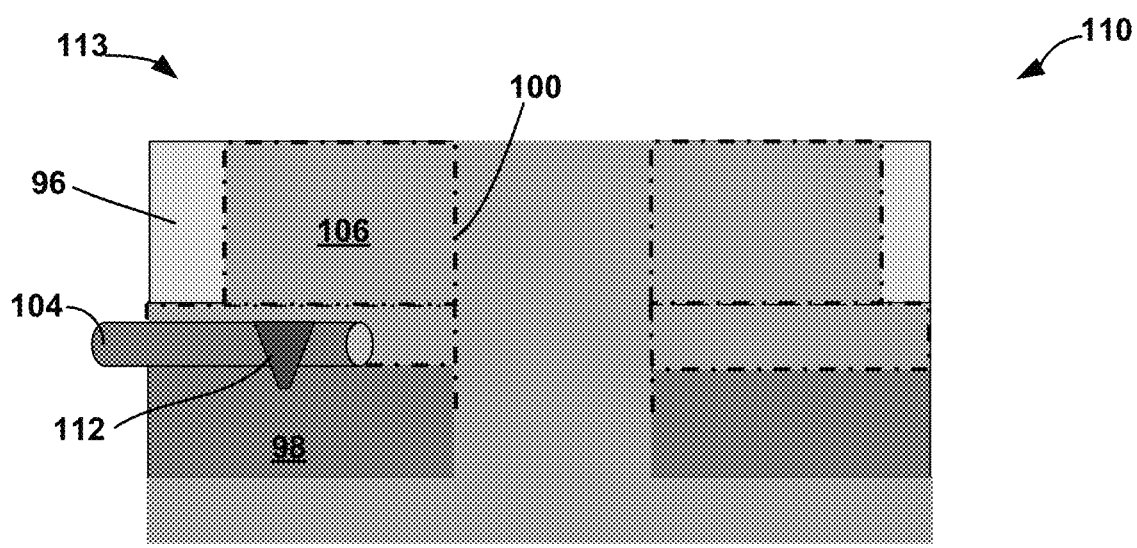

Pre-assembled electrodes such as, e.g., those electrodes formed via the techniques of FIGS. 9A-9D and 10A-10D, may be further assembled into a segmented electrode assembly for use with a medical device lead. FIG. 7 is a conceptual diagram illustrating an example segmented electrode assembly 110 including four electrodes 113-116 along a traverse cross-section. Each of electrodes 113-116 may be pre-assembled and then bonded into an electrically insulating material 118, such as, e.g., polyether ether ketone (PEEK), in the configuration shown in FIG. 7. FIG. 8 is a conceptual diagram illustrating a longitudinal cross-section of electrode 113 from electrode assembly 110. The features of electrode 113 are labeled in FIGS. 7 and 8 to correspond to the electrode formed via the technique of FIGS. 10A-10B. As shown in FIG. 8, lead wire 104 is bonded to second portion 98 via laser weld 112 within channel 102 formed in second portion 98. Electrically insulating material 106 is refilled into voids areas in channel 102 and aperture 100. Lead assembly 110 may be employed with a medical device lead, such as, leads 20 to deliver electrical stimulation to patient 12 (FIG. 1).

Figure 24:
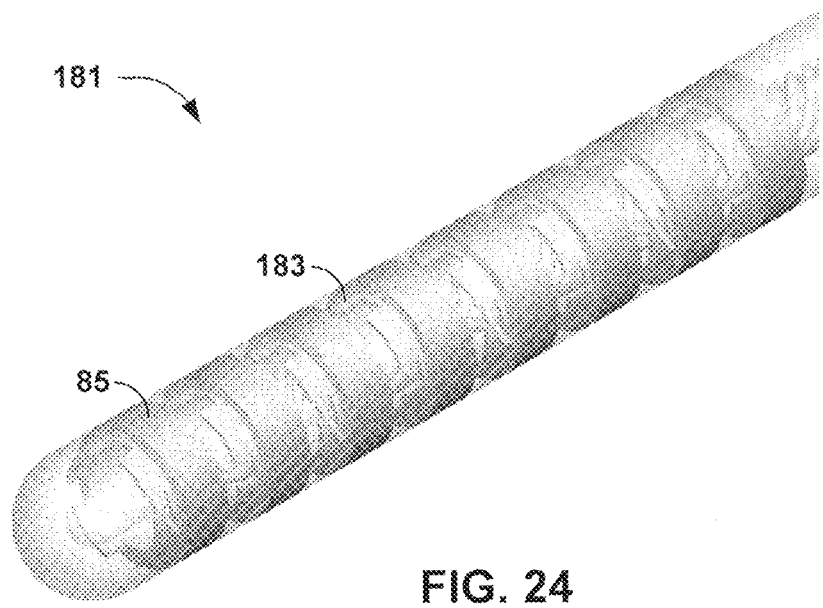
FIGS. 24-26 are conceptual diagrams illustrating another example medical lead for use in a medical device system.
Figure 25:
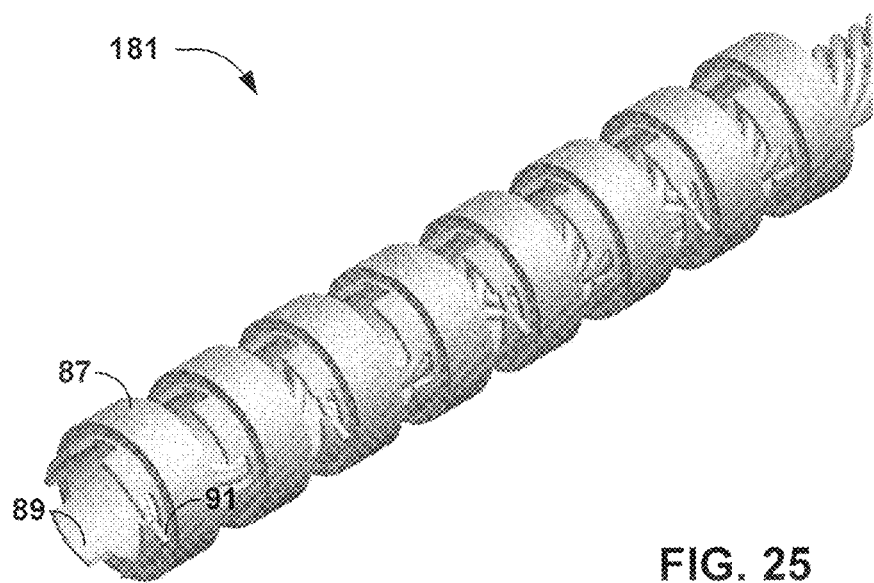
Figure 26:
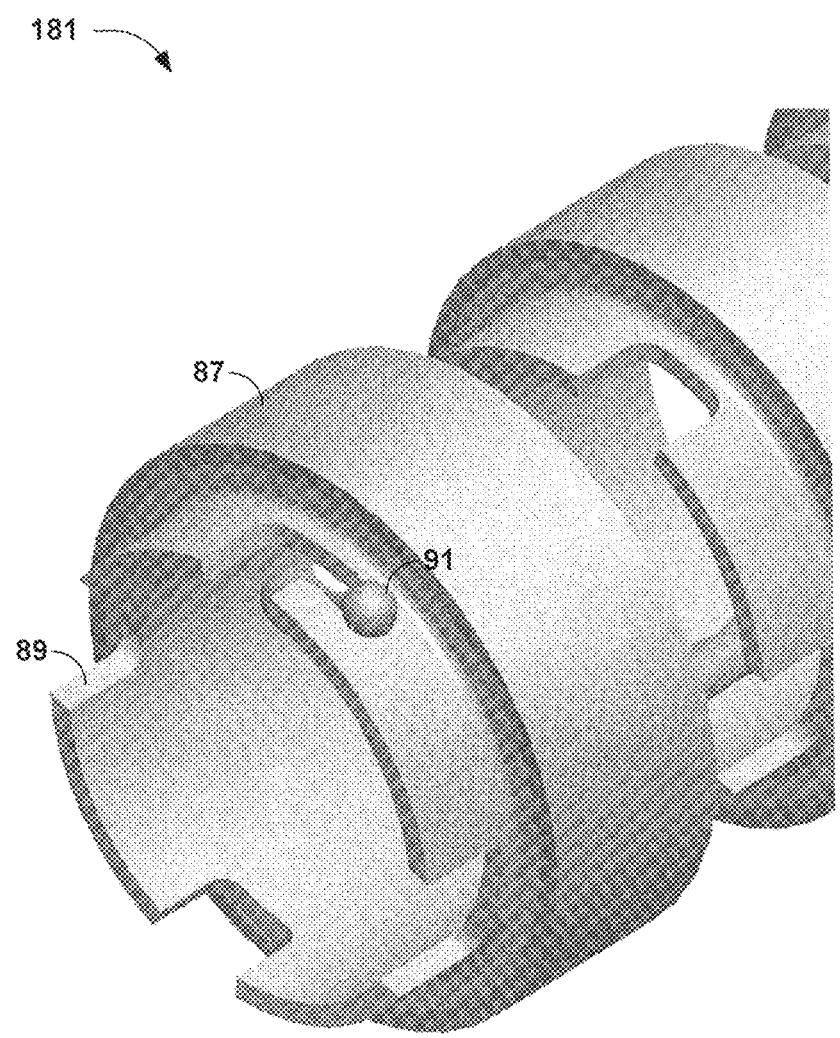

FIGS. 24-26 are conceptual diagrams illustrating another example medical lead 81 for use in a medical device system. Lead 181 includes a plurality of ring electrodes, including electrode 85 located at the end of the distal section 183 of lead 181. Electrode 85 may be substantially the same or similar to that previously described but instead of a segmented electrode, electrode 85 is a ring electrode FIG. 25 illustrates the distal end of lead 181. As shown, electrode 85 includes inner portion 89 coupled to outer portion 87. One of the plurality of lead wires of lead 181, lead wire 91, is welded or otherwise coupled to inner portion 89. Inner portion 89, outer portion 87, and lead wire 91 may be substantially similar to that of inner portion 78, outer portion 74, and lead wire 80 of lead 70 described previously.

Figure 27:
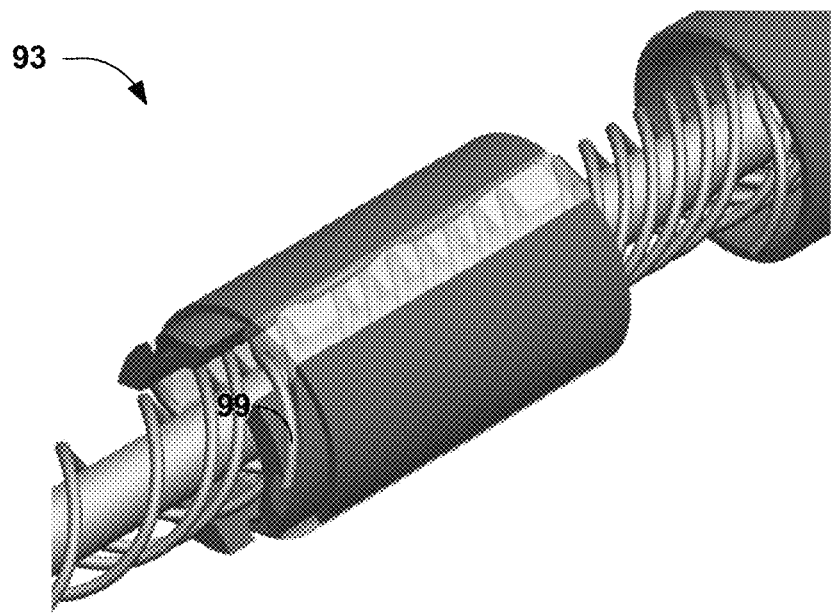
FIGS. 27-29 are conceptual diagrams illustrating another example medical lead for use in a medical device system.
Figure 28:
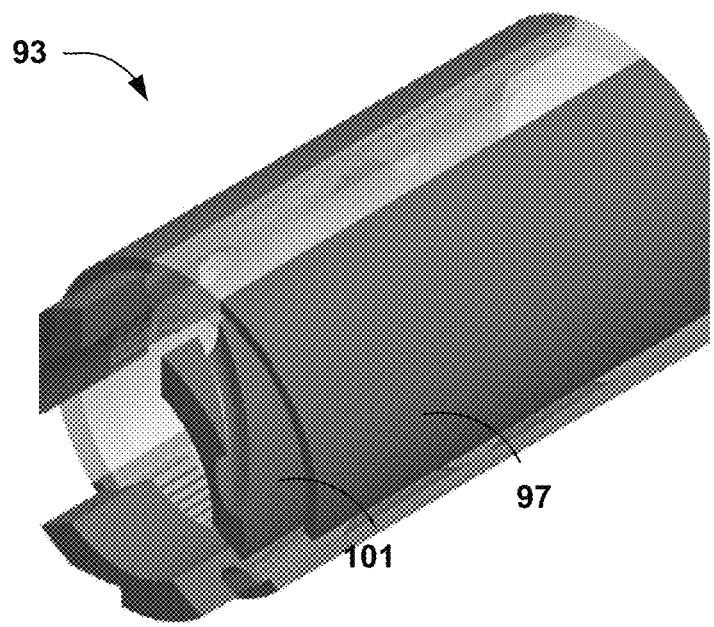
Figure 29:
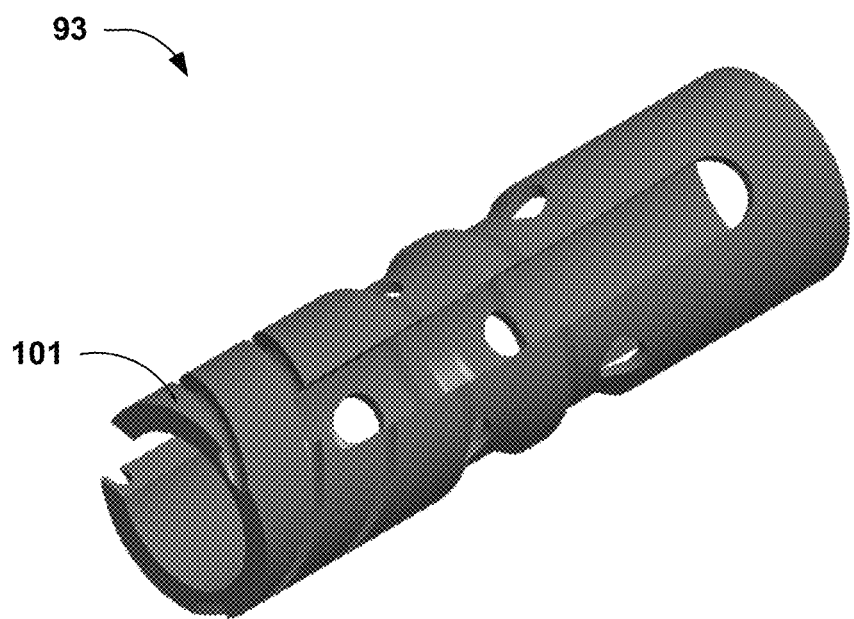

FIG. 26 is a magnified view of lead 181 showing distal electrode 85. As shown, inner portion 89 exhibits a stepped configuration with respect to the bumped surface formed by the welding of lead wire 91 to inner portion 89. In this manner, the weld bump does not protrude from the smooth circular cross section of the distal end of lead 181 after the lead body has been overmolded FIGS. 27-29 are conceptual diagrams illustrating another example medical lead 93 for use in a medical device system which may be configured in accordance in one or more examples described herein. Lead 93 is an example of a segmented electrode lead. Segmented electrode lead 93, portions of which are shown in FIG. 27-29 may be constructed using bi-metal construction. For the example of lead 93, a recessed tab 101 with the helically cut slot in the front of segmented electrode section 97 may be made from a first metal composition which is compatible to weld to the electrical conductor wire 99 shown in FIG. 27. Clad to the outer full diameter portion of the segmented electrode 97 may be a second metal composition which is preferred for direct tissue contact and electrical stimulation. FIG. 29 shows the inner section of segmented electrode 97 made from a first metal composition which is compatible with welding to the electrical conductors, such as, wire 99. The inner section also has electrode retention features and is shown in FIG. 29 before adding the second metal composition outer cladding, before insert molding with a plastic material such as PEEK, and before cutting the front and end portions away which leave discrete segmented electrode sections as shown in FIGS. 27 and 28.

EXAMPLES

A series of experiments were performed to evaluate one or more aspects related to the present disclosure. In one instance, a Ti-15Mo lead wire having a diameter of approximately 4 mils was laser welded to a Pt-10Ir connector ring. The welded sample was then polished for analysis. Nano-indentation techniques were then used to measure the hardness and modulus across the prepared sample across the welding interface. Scanning electron microscopy (SEM) and Energy Dispersive X-ray Spectroscopy (EDS) were also employed to examiner the welding interface of the sample.

Figure 11:
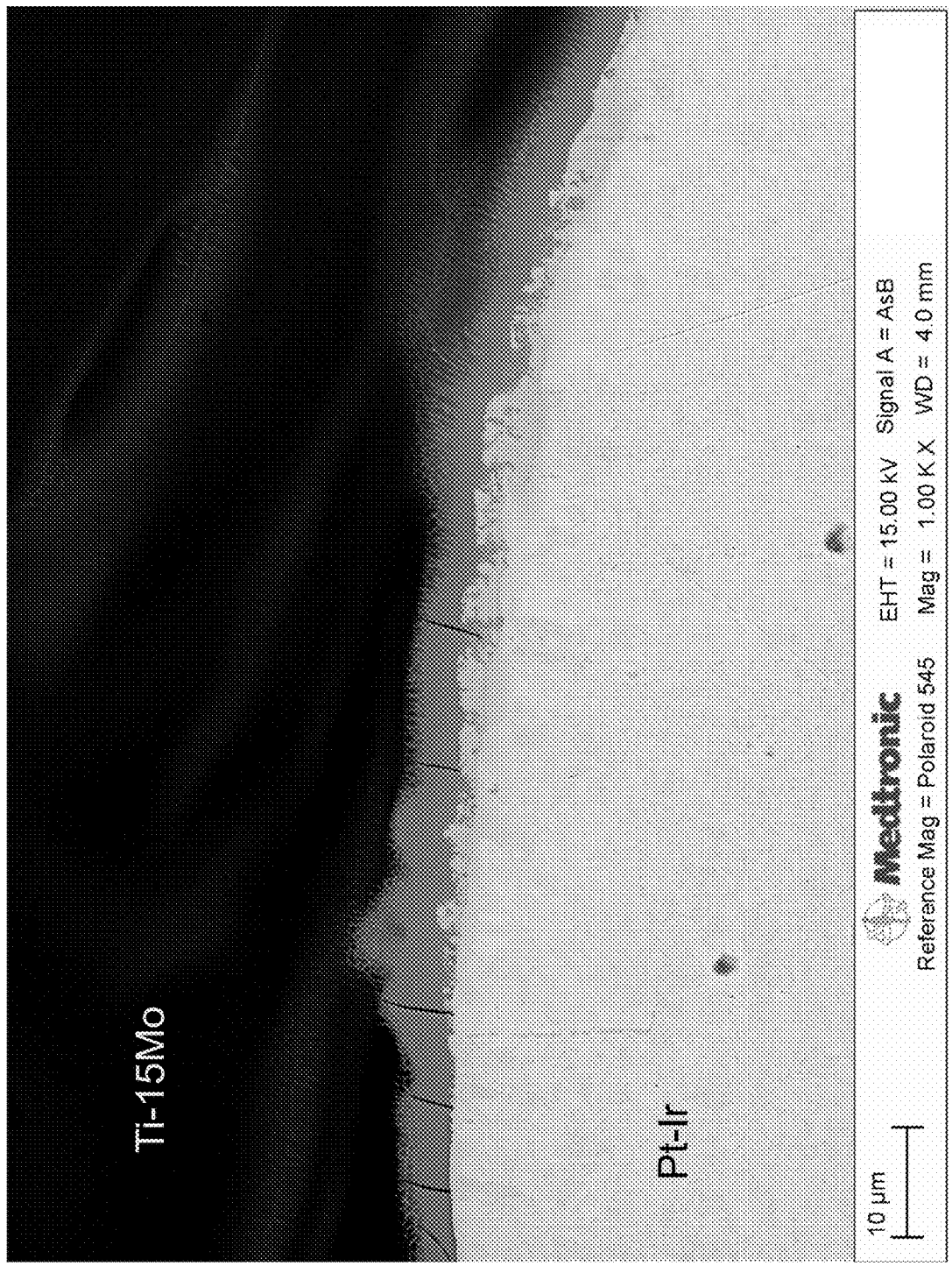
FIGS. 11-23 are various plots and images relating to experiments carried out to evaluate one or more aspects of examples of the disclosure.
Figure 12:
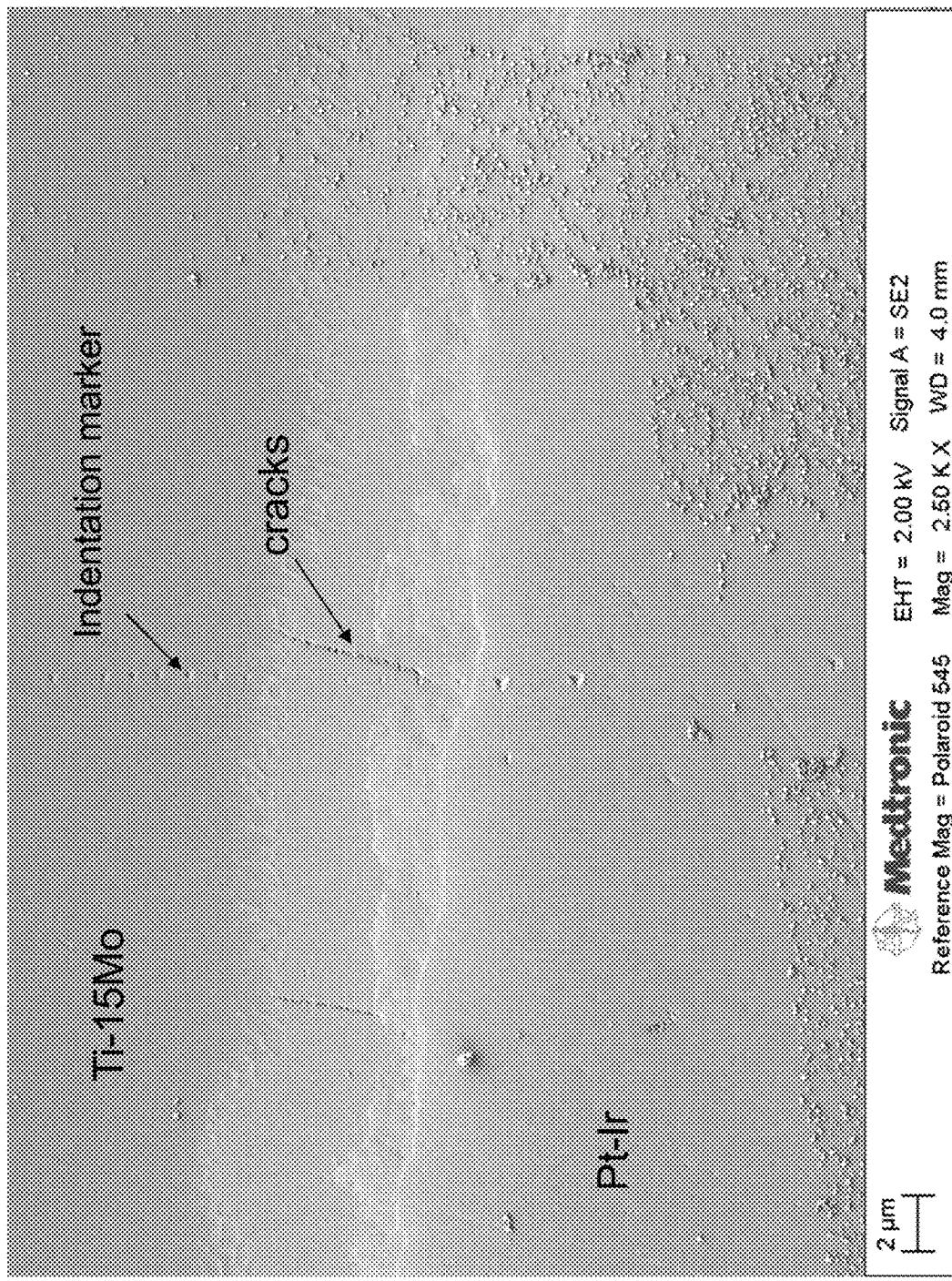

FIG. 11 is a backscattered electron image (BEI) image of the laser welding interface cross-section of Ti-15Mo wire/Pt-10Ir electrode ring sample. The image shows intermetallic materials were formed and as well as cracks in the intermetallic layer. The cracks were formed perpendicular to the interface and did not extend into either Ti-15Mo or Pt-10Ir portion of the sample FIG. 12 is a secondary electron image (SEI) of the laser welding interface cross-section of Ti-15Mo wire/Pt-10Ir electrode ring sample. The image includes nano-indentation markers as well as cracks. The size of the indent indicates the hardness of the material, the results of which are presented in FIG. 15.

Figure 13:
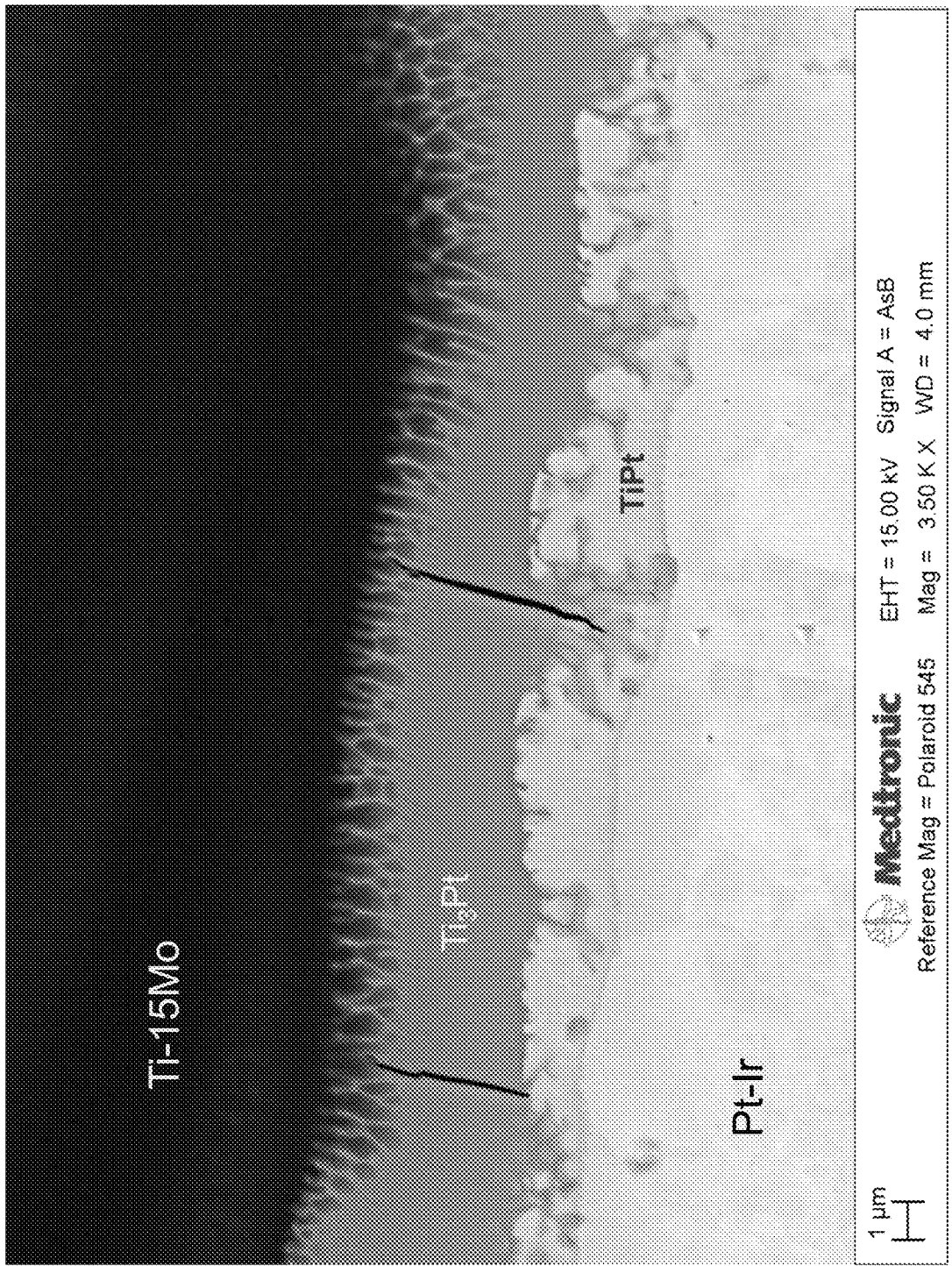

FIG. 13 is another BEI image of the laser welding interface cross-section of Ti-15Mo wire/Pt-10Ir electrode ring sample. As shown, the cracks were formed at the grey area which is a mixture of Ti-15Mo and Pt—Ir. Based on phase diagrams for a Ti/Pt material and a Ti/Mo material, the grey area was determined to be a $Ti_3Pt$ phase which also shows the dendritic structure. The light grey area was determined to be a TiPt phase.

Figure 14:
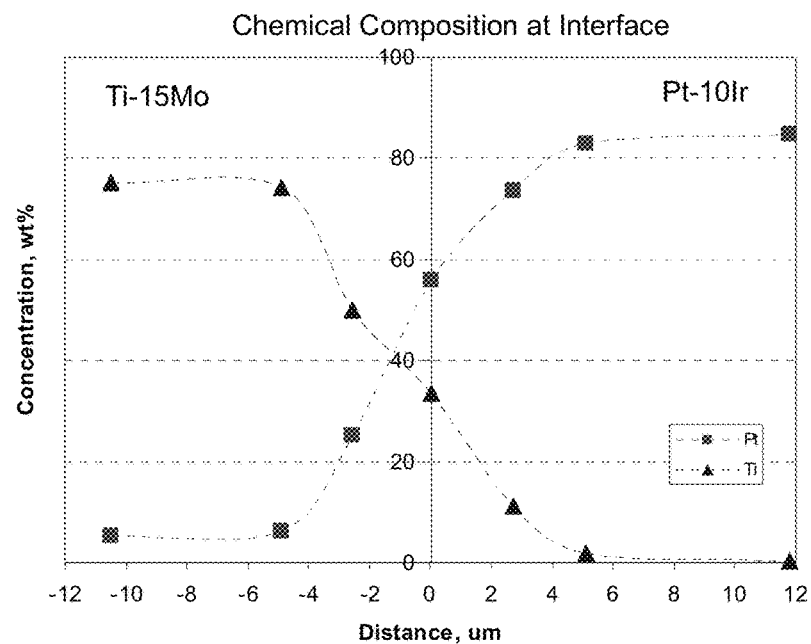

FIG. 14 is a plot illustrating the chemical composition of interface material versus the distance from the interface. As shown, the composition distribution at interface region shows a diffusion layer between the two materials of the sample at the interface.

Figure 15:
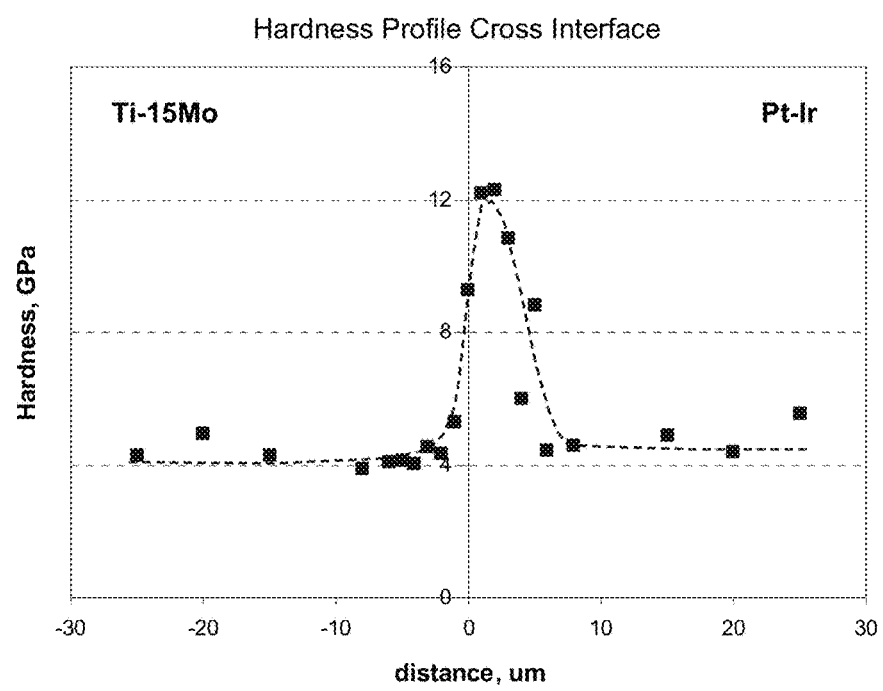

FIG. 15 is a plot illustrating the hardness of the material at the interface versus the distance from the interface. As shown by the hardness profile across the interface, the hardness of the intermetallic layer was about three times higher than the base materials of the sample.

Figure 16:
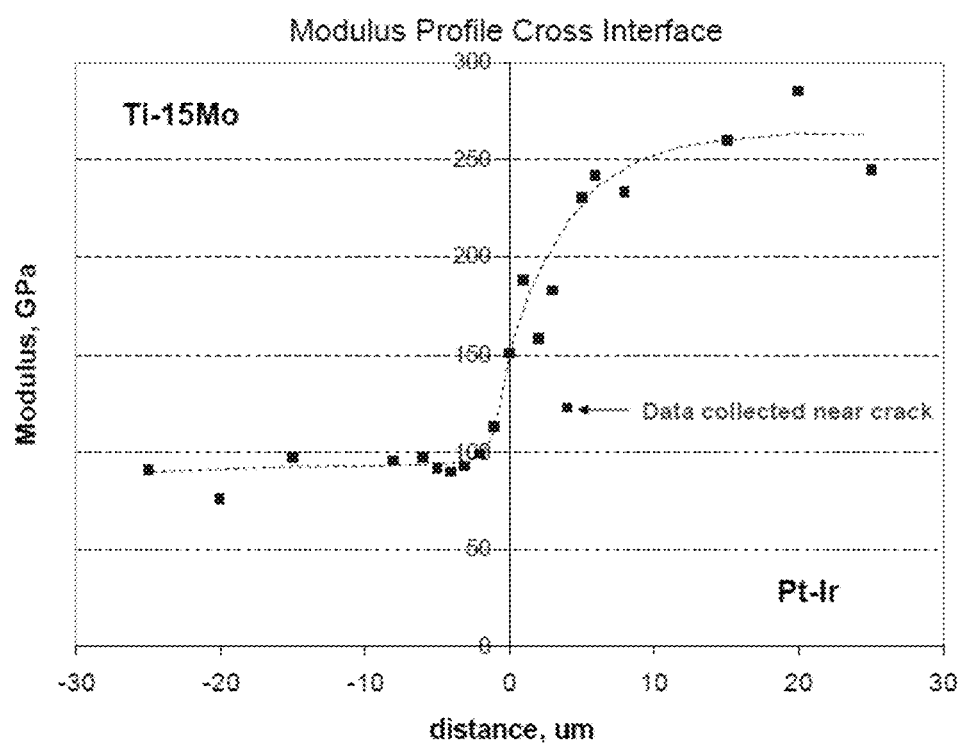

FIG. 16 is a plot illustrating the measurements of the reduced modulus using a nano-indention method of the material at the interface versus the distance from the interface. As shown by the modulus profile, the modulus gradually increased and no shape change was observed. As labeled, the data near the crack was assumed to be an abnormal value.

In general, based on the analysis of the prepared sample, it was found that the laser welding resulted in an intermetallic layer that was approximately 7 micrometers wide. Multiple cracks formed perpendicular to the interface were observed in the intermetallic layer. The hardness of the welding interface region had a shape increase, and the hardness is about three times the hardness of the Ti-15Mo region or Pt—Ir region. The modulus of the welding interface region did not have a shape increase and the modulus gradually increase moving away from the interface.

The evaluations displayed that the cracks formed in the welding zone between Ti-15Mo and Pt-10Ir and that the bonding is brittle. Accordingly, it was determined the welding is not desirable for this application. Similar results were obtained using a wide range of welding parameters both with laser welding and with resistance welding.

In another experiment, samples of Ti wire were clad with Pt-10Ir and diffusion bonding was used to bond the Ti wire to Pt-10Ir. The diffusion bonding was carried out at approximately 750 degrees Celsius, for about 30, 60, and 120 minutes at about 30 ksi Ar. The samples were then quarter cut to evaluate bond strength. Samples were also machined to test feasibility of machining. The Ti grain size in various samples was also evaluated.

Figure 17:
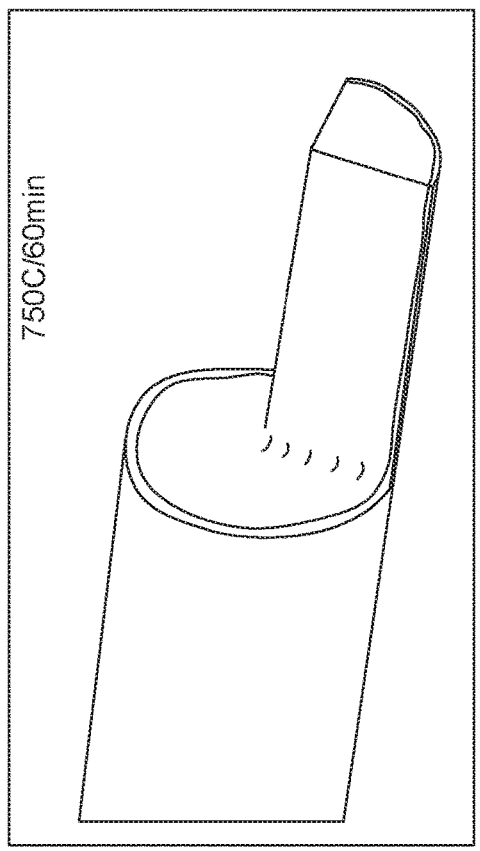
Figure 17:
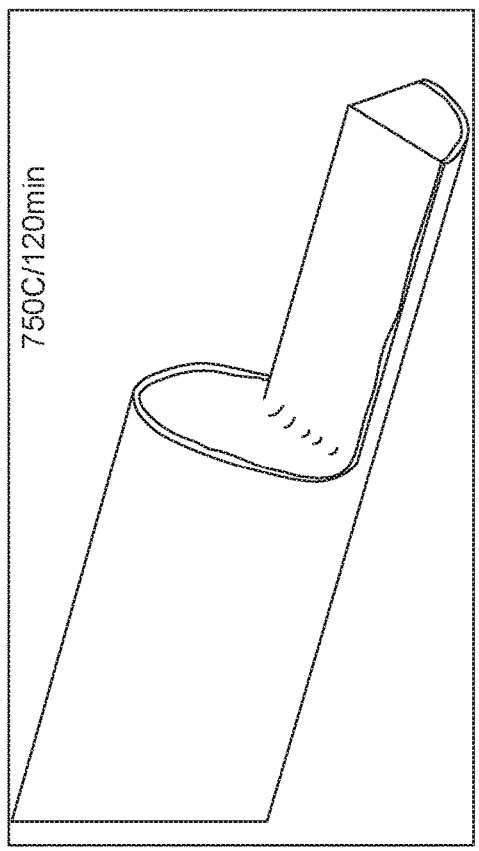
Figure 17:
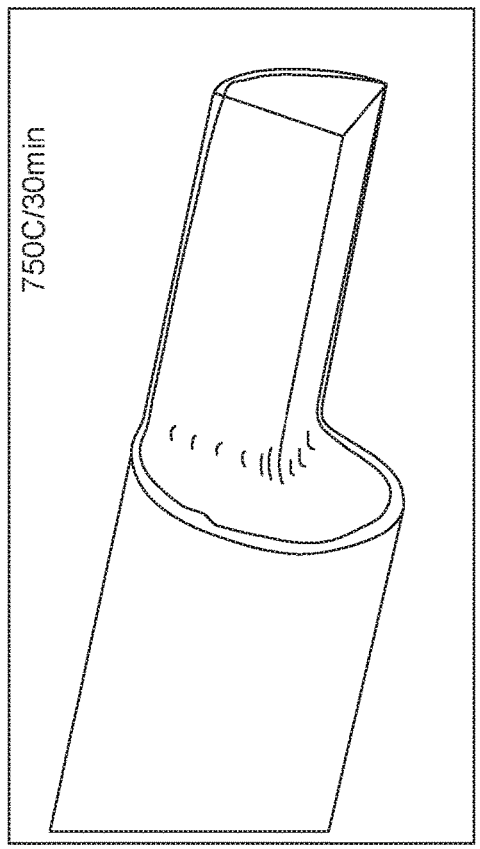
Figure 17:
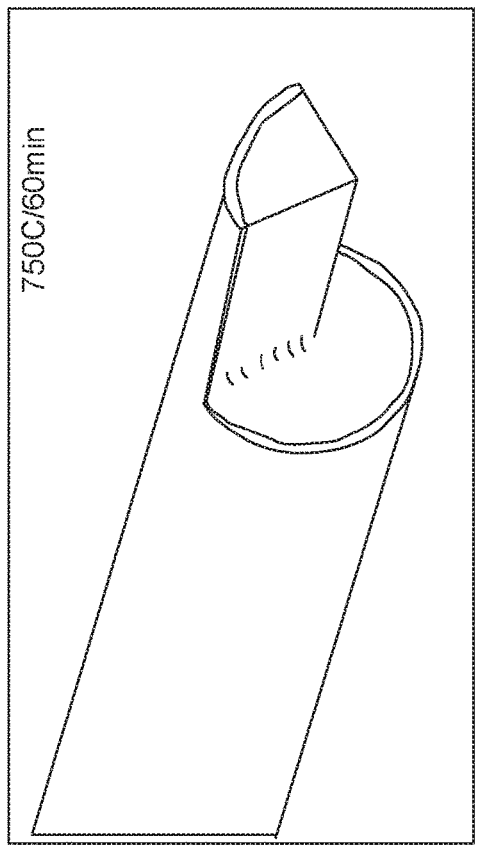

FIG. 17 is a set of four line-drawings of photographs showing various samples after being quarter cut. As shown, the sample prepared at 750 degrees Celsius for 120 minutes exhibited a bond between the Pt-10Ir and Ti rod that allowed for quarter cutting of both ends without peeling. The bond between the Pt-10Ir and Ti rod for the samples prepared at 750 degrees Celsius for 30 minutes and 60 minutes were only able to be cut at one end and with peeling.

Figure 18:
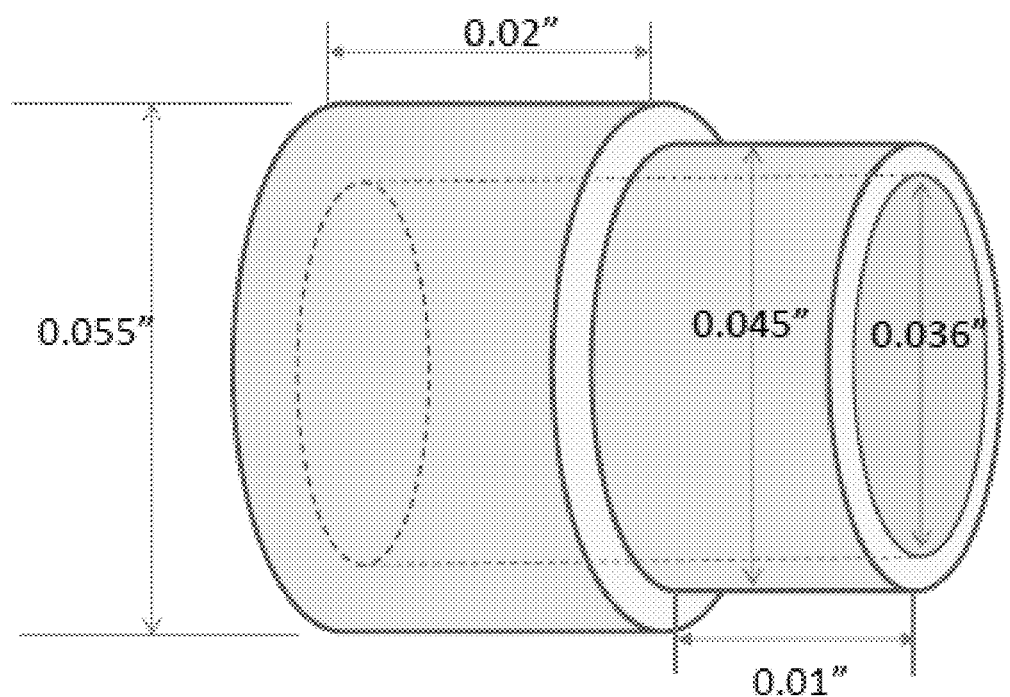

Multiple electrodes were then machined from each of the various Pt-10Ir clad/Ti rod samples. FIG. 18 is a schematic diagram illustrating the dimensions of the machined electrodes.

Figure 19:
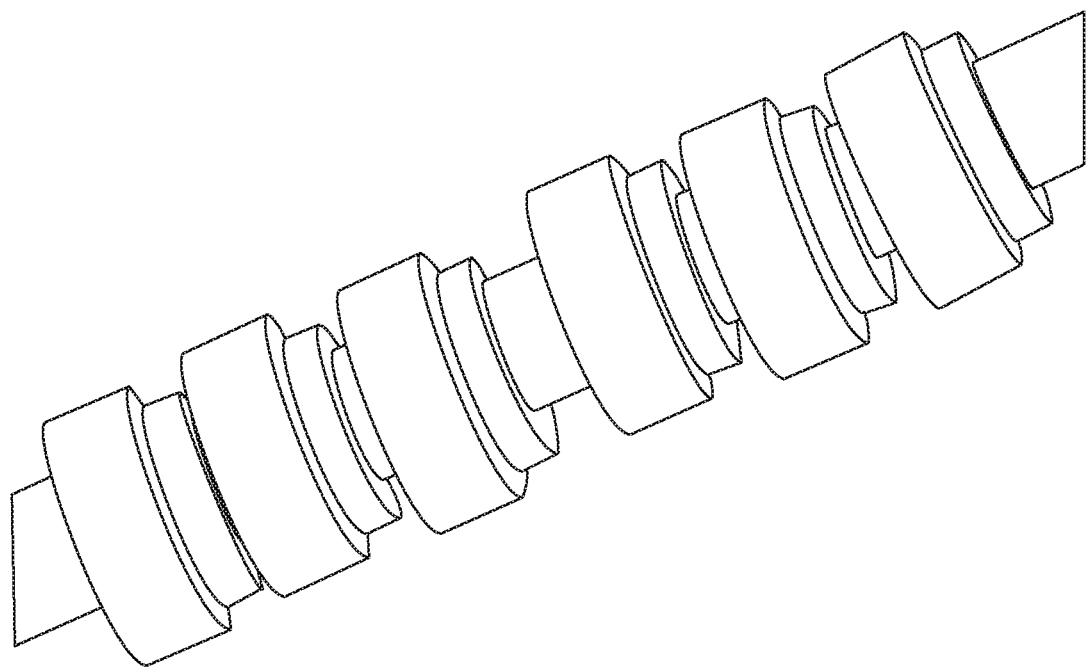

FIG. 19 is a line-drawing of a photograph showing the electrodes machined from the sample prepared at 750 degrees Celsius for 120 minutes. As shown, all electrodes where machined without any peeling.

Figure 20:
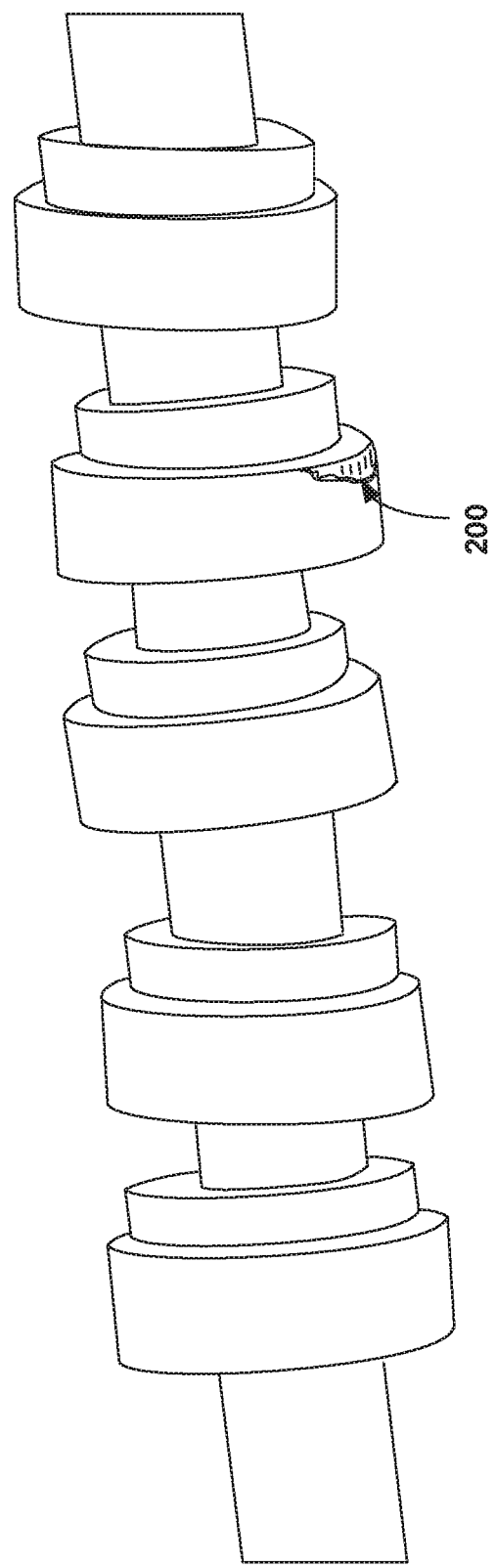

FIG. 20 is a line-drawing of a photograph showing the electrodes machined from the sample prepared at 750 degrees Celsius for 60 minutes. As shown, one of the five electrodes exhibited peeling (as indicated by the arrow 200).

Figure 21:
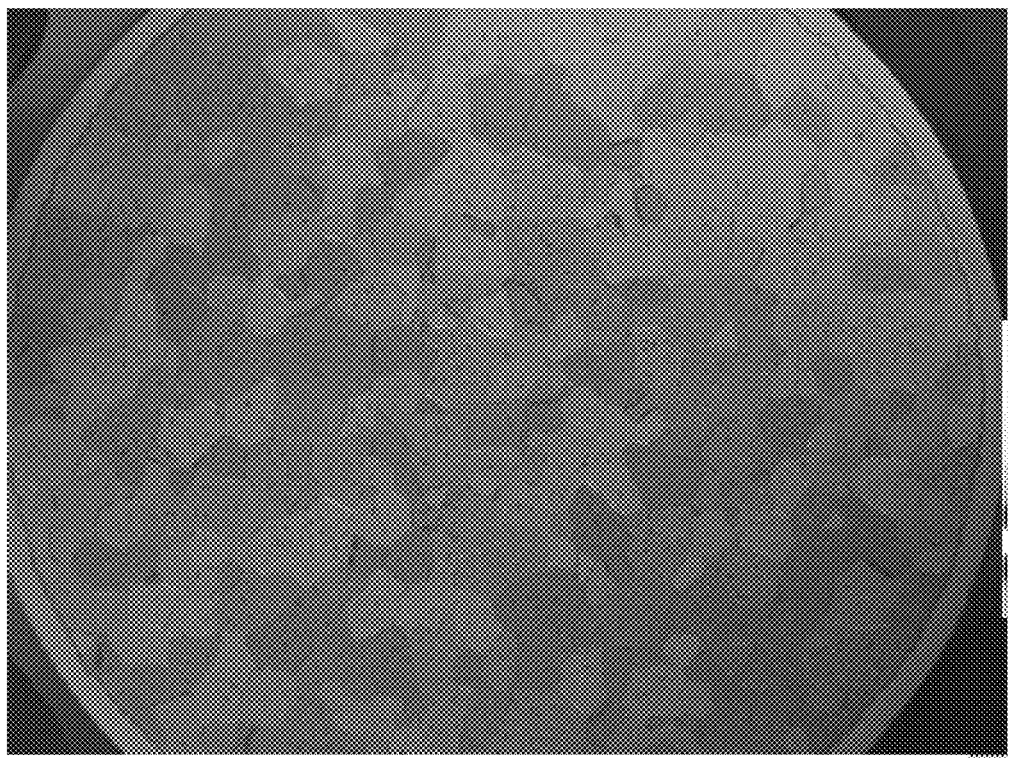
Figure 22:
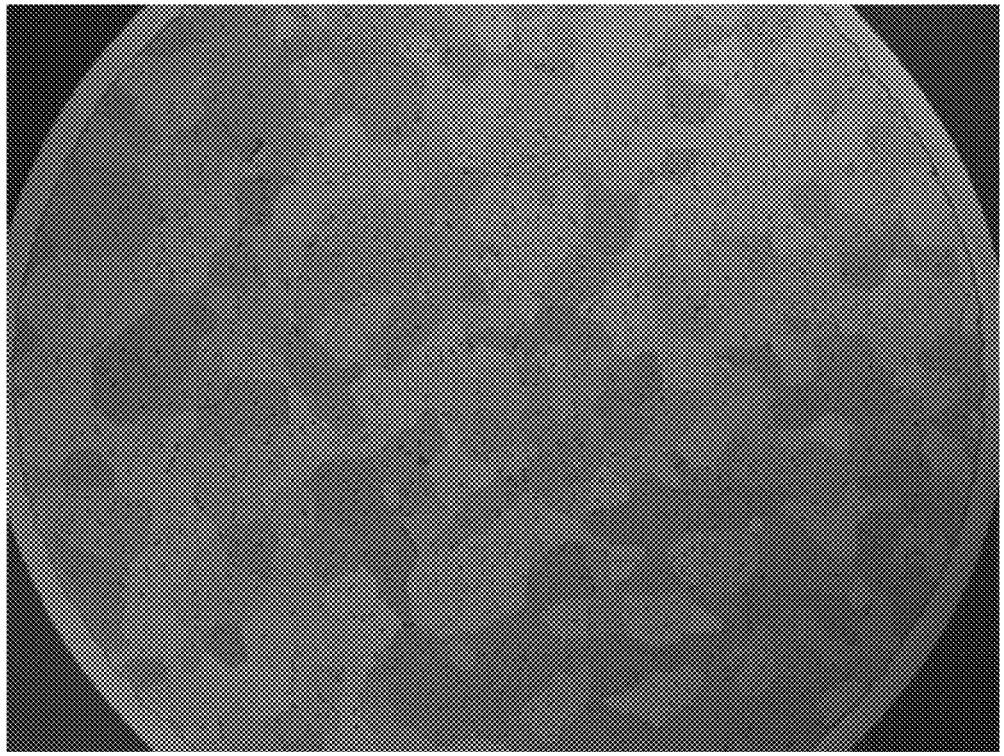

Cross-sections of various samples were then taken to evaluate Ti grain size. FIG. 21 is an image showing the cross-section of a sample prepared at 750 degrees Celsius for 120 minutes. FIG. 22 is an image showing the cross-section of a sample prepared at 750 degrees Celsius for 60 minutes. After evaluation, it was determined that the grain sizes for the samples were similar.

Figure 23:
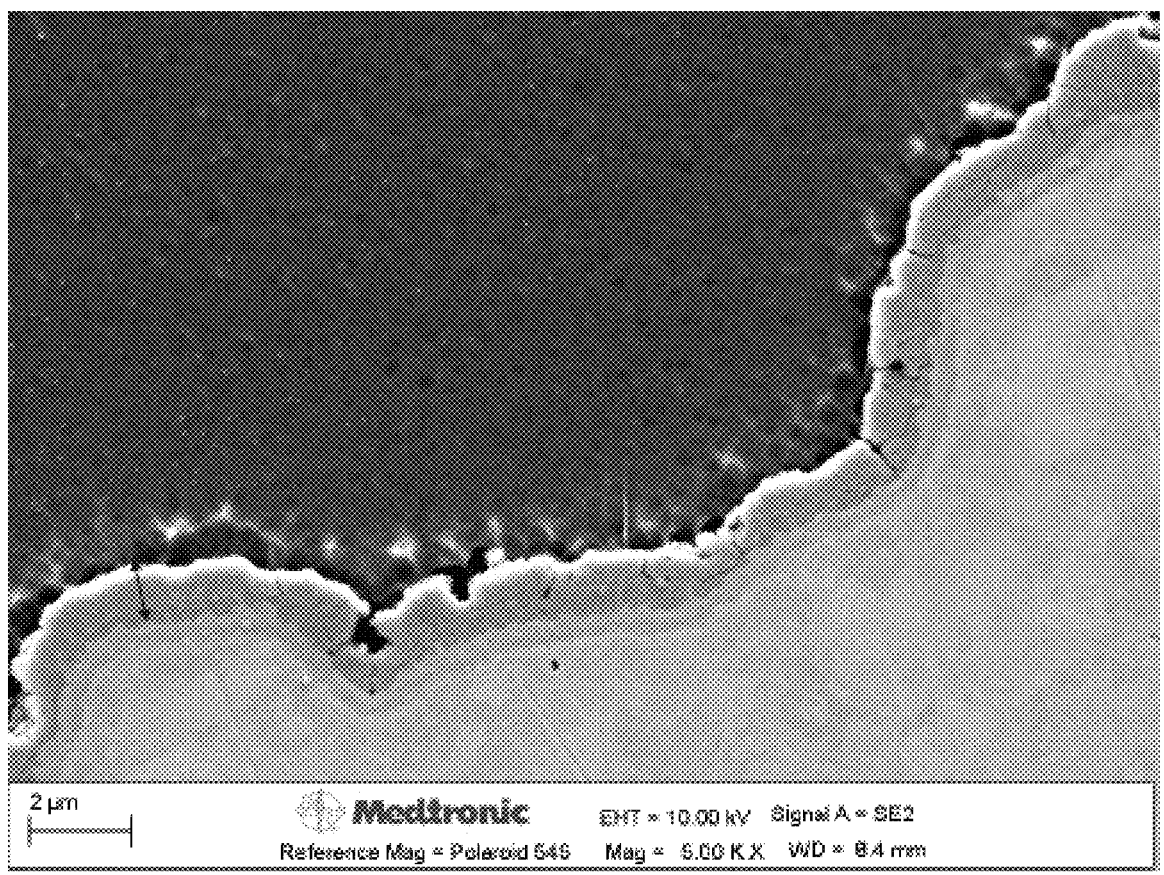

FIG. 23 is an image showing the diffusion layer at the interface between the Pt-10Ir and Ti metal of the sample prepared at 750 degrees Celsius for 120 minutes. The growth rate of the Ti rich diffusion layer due to diffusion was found to be acceptable for the 750 degrees Celsius for 120 minutes.

Various examples of the disclosure have been described. These and other examples are within the scope of the following claims.

The invention claimed is:

1. A medical device system comprising:
    a lead including an electrically conductive lead wire;
    an electrode electrically coupled to the lead wire, the electrode including a first portion and a second portion, wherein the first portion defines an exposed outer surface of the electrode and is bonded to the second portion along a first interface, wherein the second portion is electrically and mechanically coupled to the lead wire along a second interface different from the first interface via welding to couple the lead wire to the electrode, wherein the medical device system is configured to conduct an electrical signal between the lead wire and exposed outer surface of the first portion via the second portion; and
    an electrically insulating material covering an outer surface of the second portion, and
    wherein the first portion is formed from a first material having a first composition, and the second portion is formed from a second material having a second composition different from the first composition.

2. The medical device system of claim 1, wherein the lead wire is formed of a third material having a third composition, wherein the third composition is different from that of the second composition, wherein the second composition and third composition are such that the second portion is welded to the lead wire.

3. The medical device system of claim 1, wherein the second composition includes a titanium alloy.

4. The medical device system of claim 3, wherein the titanium alloy comprises titanium and molybdenum.

5. The medical device system of claim 1, wherein the first composition includes a platinum alloy.

6. The medical device system of claim 5, wherein the platinum alloy comprises platinum and iridium.

7. The medical device system of claim 1, wherein the electrically insulating material comprises at least one of polyether ether ketone and polysulfone.

8. The medical device system of claim 1, wherein the first portion and the second portion are coupled by coextrusion, hot isostatic pressing, diffusion bonding, or electromagnetic pulse technology.

9. The medical device system of claim 1, further comprising a medical device including an electrical stimulation generator, wherein the lead wire is configured to be electrically coupled to the stimulation generator such that electrical stimulation signals may be transmitted from the electrical stimulation generator across the exposed surface of the electrode via the lead wire.

10. The medical device system of claim 1, wherein the electrically insulating material covers the outer surface of the second portion such that the outer surface does not define an exposed surface of the second portion.

11. The medical device system of claim 1, wherein the first portion and second portion are electrically coupled to each other.

12. A method for forming a medical device lead, the method comprising:
    bonding a first portion of an electrode to a second portion of the electrode along a first interface, wherein the first portion defines an exposed outer surface of the electrode, wherein the first portion is formed from a first material having a first composition, and the second portion is formed from a second material having a second composition different from the first composition;
    welding the second portion to an electrically conductive lead wire of a lead to electrically and mechanically coupled to the lead wire and the second portion along a second interface different from the first interface, wherein an electrical signal may be transferred between the lead wire and exposed outer surface of the first portion via the second portion; and
    depositing an electrically insulating material to cover an outer surface of the second portion.

13. The method of claim 12, wherein the lead wire is formed of a third material having a third composition, wherein the third composition is different from that of the second composition, wherein the second composition and third composition are such that the second portion is welded to the lead wire.

14. The method of claim 12, wherein the second composition includes a titanium alloy.

15. The method of claim 14, wherein the titanium alloy comprises titanium and molybdenum.

16. The method of claim 12, wherein the first composition includes a platinum alloy.

17. The method of claim 16, wherein the platinum alloy comprises platinum and iridium.

18. The method of claim 12, wherein the electrically insulating material comprises at least one of polyether ether ketone and polysulfone.

19. The method of claim 12, wherein the first position and the second portion are coupled by coextrusion, hot isostatic pressing, diffusion bonding, or electromagnetic pulse technology.

20. The method of claim 12, further comprising electrically coupling the lead wire to a stimulation generator of a medical device such that electrical stimulation signals may be transmitted from the electrical stimulation generator across the exposed surface of the electrode via the lead wire.

\* \* \* \* \*